United States Patent [19]
Metz et al.

[11] Patent Number: 5,445,947
[45] Date of Patent: Aug. 29, 1995

[54] JOJOBA WAX BIOSYNTHESIS GENE

[75] Inventors: James G. Metz, Davis; Kathryn D. Lardizabal, Woodland; Michael W. Lassner, Davis, all of Calif.

[73] Assignee: Calgene Inc., Davis, Calif.

[21] Appl. No.: 66,299

[22] Filed: May 20, 1993

Related U.S. Application Data

[63] Continuation-in-part of Ser. No. 796,256, Nov. 20, 1991, abandoned, and a continuation-in-part of Ser. No. 933,411, Aug. 21, 1992, abandoned and a continuation-in-part of PCT/US92/09863 filed Nov. 13, 1992.

[51] Int. Cl.$^6$ .......................... C12P 1/04; C12P 7/64; A01M 1/00; C12N 15/05
[52] U.S. Cl. ................................. 435/69.1; 435/71.2; 435/134; 435/172.3; 435/240.4; 536/23.6; 536/23.2; 800/200; 800/205; 800/255; 800/DIG. 17
[58] Field of Search ................... 435/69.1, 70.1, 240.4, 435/252.3, 172.1, 172.3, 71.2; 536/23.6, 23.2; 800/200, 250, 255, DIG. 17, 205

[56] References Cited

U.S. PATENT DOCUMENTS 4,826,767 5/1989 Hansen et al. ........................ 435/134

FOREIGN PATENT DOCUMENTS 0255378 2/1988 European Pat. Off. .

OTHER PUBLICATIONS

Potrykus, I. 1991, Annu. Rev. Plant Physiol. Plant Mol. Biol. 43:205–225.
Matsuda et al. 1981. FEBS Letters. 126(1):111–113.
Sambrook et al. 1989. Molecular Cloning-A Laboratory Manual. Second Edition. pp. 11.1–11.19; 11.45–11.49; 11.52–11.61.
Anderson, et al., "Characterization of Enzymes Involved In in Biosynthesis of Long Chain Liquid Waxes of Jojoba (*Simmondsia chinensis*)," *Plant Physiology* (1992) 99:77 abstract.
Kolattukudy and Rogers, "Acyl–CoA Reductase and Acyl–CoA: Fatty Alcohol Acyl Transferase in the Microsomal Preparation From The Bovine Meibomian Gland," *J. of Lipid Research* (1986) 27:404–411.
Pollard, et al., "Studies on Biosynthesis of Waxes by Developing Seed. II. The Demonstration of Wax Biosynthesis by Cell–Free Homogenates," *Lipids* (1979) 14(7):651–662.
Pushnik, et al., "Characterization of the Biosynthetic Pathway For Formation of Liquid Wax in Jojoba," abstract The Southwest Consortium Fourth Annual Meeting, Feb. 7, 1989.
Wilder, G. and Hallick, R., "Wax Ester Biosynthesis in *Euglena gracilis*," abstract The Southwest Consortium Fifth Annual Meeting, Apr. 22–24, 1990.
Wu, et al., "Studies of Biosynthesis of Waxes by Developing Jojoba Seed: III. Biosynthesis of Wax Esters from Acyl–Coa and Long Chain Alcohols," *Lipids* (1981) 16(12):897–902.
Yamauchi, et al., "Purification and Characterization of Acyl Coenzyme A: Alcohol Acyltransferase of Neurospora sp.," *Agric. Biol. Chem.* (1989) 53(6):1551–1556.

*Primary Examiner*—David T. Fox
*Assistant Examiner*—Erich E. Veitenheimer

[57] ABSTRACT

By this invention, a partially purified fatty acyl-CoA: fatty alcohol acyltransferase (wax synthase) is provided, wherein said protein is active in the formation of a wax ester from fatty alcohol and fatty acyl substrates. Of special interest is a jojoba embryo wax synthase having an apparent molecular mass of approximately 57 kD. Also considered are amino acid and nucleic acid sequences obtainable from wax synthase proteins and the use of such sequences to provide transgenic host cells capable of producing wax esters.

10 Claims, 21 Drawing Sheets

```
AAATCCTCCA CTCATACACT CCACTTCTCT CTCTCTCTCT CTCTCTCTGA AACAATTTGA      60

GTAGCAAACT TAAAAGAAA ATG GAG GAA ATG GGA AGC ATT TTA GAG TTT CTT     112
                     Met Glu Glu Met Gly Ser Ile Leu Glu Phe Leu
                      1               5                      10

GAT AAC AAA GCC ATT TTG GTC ACT GGT GCT ACT GGC TCC TTA GCA AAA      160
Asp Asn Lys Ala Ile Leu Val Thr Gly Ala Thr Gly Ser Leu Ala Lys
             15                      20                      25

ATT TTT GTG GAG AAG GTA CTG AGG AGT CAA CCG AAT GTG AAG AAA CTC      208
Ile Phe Val Glu Lys Val Leu Arg Ser Gln Pro Asn Val Lys Lys Leu
             30                      35                      40

TAT CTT CTT TTG AGA GCA ACC GAT GAC GAG ACA GCT GCT CTA CGC TTG      256
Tyr Leu Leu Leu Arg Ala Thr Asp Asp Glu Thr Ala Ala Leu Arg Leu
             45                      50                      55

CAA AAT GAG GTT TTT GGA AAA GAG TTG GGA AAA TTT AAA GTT CTG AAA CAA AAT  304
Gln Asn Glu Val Phe Gly Lys Glu Leu Gly Lys Phe Lys Val Leu Lys Gln Asn
             60                      65                      70                      75
```

```
TTA GGT GCA AAT TTC TAT TCC TTT GTA TCA GAA AAA GTG ACT GTA GTA    352
Leu Gly Ala Asn Phe Tyr Ser Phe Val Ser Glu Lys Val Thr Val Val
            80                      85                  90

CCC GGT GAT ATT ACT GGT GAA GAC TTG TGT CTC AAA GAC GTC AAT TTG    400
Pro Gly Asp Ile Thr Gly Glu Asp Leu Cys Leu Lys Asp Val Asn Leu
                95                     100                 105

AAG GAA GAA ATG TGG AGG GAA ATC GAT GTT GTT AAT CTA GCT GCT        448
Lys Glu Glu Met Trp Arg Glu Ile Asp Val Val Asn Leu Ala Ala
            110                  115                 120

ACA ATC AAC TTC ATT GAA AGG TAC GAC GTG TCT CTG CTT ATC AAC ACA    496
Thr Ile Asn Phe Ile Glu Arg Tyr Asp Val Ser Leu Leu Ile Asn Thr
            125                 130                 135

TAT GGA GCC AAG TAT GTT TTG GAC TTC GCG AAG AAG TGC AAC AAA TTA    544
Tyr Gly Ala Lys Tyr Val Leu Asp Phe Ala Lys Lys Cys Asn Lys Leu
            140                 145                 150         155

AAG ATA TTT GTT CAT GTA TCT ACT GCT TAT GTA TCT GGA GAG AAA AAT    592
Lys Ile Phe Val His Val Ser Thr Ala Tyr Val Ser Gly Glu Lys Asn
            160                 165                 170
```

```
GGG TTA ATA CTG GAG AAG CCT TAT TAT ATG GGC GAG TCA CTT AAT GGA      640
Gly Leu Ile Leu Glu Lys Pro Tyr Tyr Met Gly Glu Ser Leu Asn Gly
            175                 180                 185

AGA TTA GGT CTG GAC ATT AAT GTA GAG AAG AAA CTT GTG GAG GCA AAA      688
Arg Leu Gly Leu Asp Ile Asn Val Glu Lys Lys Leu Val Glu Ala Lys
            190                 195                 200

ATC AAT GAA CTT CAA GCA GCG GGG GCA ACG GAA AAG TCC ATT AAA TCG      736
Ile Asn Glu Leu Gln Ala Ala Gly Ala Thr Glu Lys Ser Ile Lys Ser
            205                 210                 215

ACA ATG AAG GAC ATG GGC ATC GAG AGG GCA AGA CAC TGG GGA TGG CCA      784
Thr Met Lys Asp Met Gly Ile Glu Arg Ala Arg His Trp Gly Trp Pro
220                 225                 230                 235

AAT GTG TAT GTA TTC ACC AAG GCA TTA GGG GAG ATG CTT TTG ATG CAA      832
Asn Val Tyr Val Phe Thr Lys Ala Leu Gly Glu Met Leu Leu Met Gln
                240                 245                 250

TAC AAA GGG GAC ATT CCG CTT ACT ATT ATT CGT CCC ACC ATC ATC ACC      880
Tyr Lys Gly Asp Ile Pro Leu Thr Ile Ile Arg Pro Thr Ile Ile Thr
        255                 260                 265
```

FIG. 1C

| | | | | | | | | |
|---|---|---|---|---|---|---|---|---|
| AGC | ACT | TTT | AAA | GAG | CCC | TTT | CCT | GGT | TGG | GTT | GAA | GGT | GTC | AGG | ACC | 928 |
| Ser | Thr | Phe | Lys | Glu | Pro | Phe | Pro | Gly | Trp | Val | Glu | Gly | Val | Arg | Thr | |
| 270 | | | | | | 275 | | | | 280 | | | | | | |

AGC ACT TTT AAA GAG CCC TTT CCT GGT TGG GTT GAA GGT GTC AGG ACC    928
Ser Thr Phe Lys Glu Pro Phe Pro Gly Trp Val Glu Gly Val Arg Thr
270                     275                 280

ATC GAT AAT GTA CCT GTA TAT TAT GGT AAA GGG AGA TTG AGG TGT ATG    976
Ile Asp Asn Val Pro Val Tyr Tyr Gly Lys Gly Arg Leu Arg Cys Met
        285                 290                 295

CTT TGC GGA CCC AGC ACA ATA ATT GAC CTG ATA CCG GCA GAT ATG GTC   1024
Leu Cys Gly Pro Ser Thr Ile Ile Asp Leu Ile Pro Ala Asp Met Val
300                 305                 310                 315

GTG AAT GCA ACG ATA GTA GCC ATG GTG GCG CAC GCA AAC CAA AGA TAC   1072
Val Asn Ala Thr Ile Val Ala Met Val Ala His Ala Asn Gln Arg Tyr
        320                 325                 330

GTA GAG CCG GTG ACA TAC CAT GTG GGA TCT TCA GCG GCG AAT CCA ATG   1120
Val Glu Pro Val Thr Tyr His Val Gly Ser Ser Ala Ala Asn Pro Met
            335                 340                 345

AAA CTG AGT GCA TTA CCA GAG ATG GCA CAC CGT TAC TTC ACC AAG AAT   1168
Lys Leu Ser Ala Leu Pro Glu Met Ala His Arg Tyr Phe Thr Lys Asn
350                 355                 360

FIG. 1D

```
CCA TGG ATC AAC CCG GAT CGC AAC CCA GTA CAT GTG GGT CGG GCT ATG    1216
Pro Trp Ile Asn Pro Asp Arg Asn Pro Val His Val Gly Arg Ala Met
365                 370                 375

GTC TTC TCC TTC TCC ACC TTC CAC CTT TAT CTC ACC CTT AAT TTC        1264
Val Phe Ser Phe Ser Thr Phe His Leu Tyr Leu Thr Leu Asn Phe
    380                 385                 390             395

CTC CTT CCT TTG AAG GTA CTG GAG ATA GCA AAT ACA ATA TTC TGC CAA    1312
Leu Leu Pro Leu Lys Val Leu Glu Ile Ala Asn Thr Ile Phe Cys Gln
                400                 405                 410

TGG TTC AAG GGT AAG TAC ATG GAT CTT AAA AGG AAG ACG AGG TTG TTG    1360
Trp Phe Lys Gly Lys Tyr Met Asp Leu Lys Arg Lys Thr Arg Leu Leu
            415                 420                 425

TTG CGT TTA GTA GAC ATT TAT AAA CCC TAC CTC TTC TTC CAA GGC ATC    1408
Leu Arg Leu Val Asp Ile Tyr Lys Pro Tyr Leu Phe Phe Gln Gly Ile
        430                 435                 440

TTT GAT GAC ATG AAC ACT GAG AAG TTG CGG ATT GCT GCA AAA GAA AGC    1456
Phe Asp Asp Met Asn Thr Glu Lys Leu Arg Ile Ala Ala Lys Glu Ser
445                 450                 455
```

FIG. 1E

```
ATA GTT GAA GCT GAT ATG TTT TAC TTT GAT CCC AGG GCA ATT AAC TGG    1504
Ile Val Glu Ala Asp Met Phe Tyr Phe Asp Pro Arg Ala Ile Asn Trp
460                 465                 470                 475

GAA GAT TAC TTC TTG AAA ACT CAT TTC CCA GGN GTC GTA GAG CAC GTT    1552
Glu Asp Tyr Phe Leu Lys Thr His Phe Pro Gly Val Val Glu His Val
                480                 485                 490

CTT AAC TAAAAGTTAC GGTACGAAAA TGAGAAGATT GGAATGCATG CACCGAAAGN    1608
Leu Asn

NCAACATAAA AGACGTGGTT AAAGTCATGG TCAAAAAAGA AATAAAATGC AGTTAGGTTT  1668

GTGTTGCAGT TTTGATTCCT TGTATTGTTA CTTGTACTTT TGATCTTTTT CTTTTTTAAT  1728

GAAATTCTC TCTTTGTTTT GTGAAAAAAA AAAAAAAAAA GAGCTCCTGC AGAAGCTT    1786
```

FIG. 1F

GGAACTCCAT CCCTTCCTCC CTCACTCCTC TCTCTACA ATG AAG GCC AAA ACA ATC 56
                                         Met Lys Ala Lys Thr Ile
                                          1                    5

ACA AAC CCG GAG ATC CAA GTC TCC ACG ACC ATG ACC ACG ACC ACG 104
Thr Asn Pro Glu Ile Gln Val Ser Thr Thr Met Thr Thr Thr Thr
         10                  15                  20

ACT ATG ACC GCC ACT CTC CCC AAC TTC AAG TCC TCC ATC AAC TTA CAC 152
Thr Met Thr Ala Thr Leu Pro Asn Phe Lys Ser Ser Ile Asn Leu His
         25                  30                  35

CAC GTC AAG CTC GGC TAC CAC TAC TTA ATC TCC AAT GCC CTC TTC CTC 200
His Val Lys Leu Gly Tyr His Tyr Leu Ile Ser Asn Ala Leu Phe Leu
         40                  45                  50

GTA TTC ATC CCC CTT TTG GGC CTC GCT TCG GCC CAT CTC TCC TCC TTC 248
Val Phe Ile Pro Leu Leu Gly Leu Ala Ser Ala His Leu Ser Ser Phe
         55                  60                  65             70

FIG. 2A

```
TCG GCC CAT GAC TTG TCC CTG CTC TTC GAC CTC CGC AAC CTC      296
Ser Ala His Asp Leu Ser Leu Leu Phe Asp Leu Arg Asn Leu
                75                  80                  85

CTC CCT GTT GTC GTT TGT TCT TTC CTC TTC GTT TTA GCA ACC CTA  344
Leu Pro Val Val Val Cys Ser Phe Leu Phe Val Leu Ala Thr Leu
        90                  95                 100

CAT TTC ACC CGG CCC AGG AAT GTC TAC TTG GAC TTT GGA TGC      392
His Phe Thr Arg Pro Arg Asn Val Tyr Leu Val Asp Phe Gly Cys
            105                 110                 115

TAT AAG CCT CAA CCG AAC CTG ATG ACA TCC CAC GAG ATG TTC ATG GAC  440
Tyr Lys Pro Gln Pro Asn Leu Met Thr Ser His Glu Met Phe Met Asp
        120                 125                 130

CGG ACC TCC CGG GCC GGG TCG TTT TCT AAG GAG AAT ATT GAG TTT CAG  488
Arg Thr Ser Arg Ala Gly Ser Phe Ser Lys Glu Asn Ile Glu Phe Gln
    135                 140                 145                 150

AGG AAG ATC TTG GAG AGG GCC GGT ATG GGT CGG GAA ACC TAT GTC CCC  536
Arg Lys Ile Leu Glu Arg Ala Gly Met Gly Arg Glu Thr Tyr Val Pro
                155                 160                 165
```

FIG. 2B

```
GAA TCC GTC ACT AAG GTG CCC GCC GAG CCG AGC ATA GCA GCA GCC AGG    584
Glu Ser Val Thr Lys Val Pro Ala Glu Pro Ser Ile Ala Ala Ala Arg
            170                 175                 180

GCC GAG GCG GAG GAG GTG ATG TAC GGG GCG ATC GAC GAG GTG TTG GAG    632
Ala Glu Ala Glu Glu Val Met Tyr Gly Ala Ile Asp Glu Val Leu Glu
        185                 190                 195

AAG ACG GGG GTG AAG CCG AAG CAG ATA GGA ATA CTG GTG GTG ANC TGC    680
Lys Thr Gly Val Lys Pro Lys Gln Ile Gly Ile Leu Val Val Xxx Cys
            200                 205                 210

AGC TTG TTT AAC CCA ACG CCG TCG CTG TCA TCC ATG ATA GTT AAC CAT    728
Ser Leu Phe Asn Pro Thr Pro Ser Leu Ser Ser Met Ile Val Asn His
        215                 220                 225                 230

TAC AAG CTN AGG GGT AAT ATA CTT AGC TAT AAT CTT GGT GGC ATG GGT    776
Tyr Lys Leu Arg Gly Asn Ile Leu Ser Tyr Asn Leu Gly Gly Met Gly
            235                 240                 245

TGC AGT GCT GGG CTC ATT TCC ATT GAT CTT GCC AAG GAC CTC CTA CAG    824
Cys Ser Ala Gly Leu Ile Ser Ile Asp Leu Ala Lys Asp Leu Leu Gln
        250                 255                 260
```

FIG. 2C

```
GTT TAC CGT AAA AAC ACA TAT GTG TTA GTA GTG AGC ACG GAA AAC ATG      872
Val Tyr Arg Lys Asn Thr Tyr Val Leu Val Val Ser Thr Glu Asn Met
265                 270                 275

ACC CTT AAT TGG TAC TGG GGC AAT GAC CGC TCC ATG CTT ATC ACC AAC      920
Thr Leu Asn Trp Tyr Trp Gly Asn Asp Arg Ser Met Leu Ile Thr Asn
        280                 285                 290

TGC CTA TTT CGC ATG GGT GGC GCT GCC ATC ATC CTC TCA AAC CGC TGG      968
Cys Leu Phe Arg Met Gly Gly Ala Ala Ile Ile Leu Ser Asn Arg Trp
295                 300                 305                 310

CGT GAT CGT CGC CGA TCC AAG TAC CAA CTC CTT CAT ACA GTA CGC ACC     1016
Arg Asp Arg Arg Arg Ser Lys Tyr Gln Leu Leu His Thr Val Arg Thr
        315                 320                 325

CAC AAG GGC GAC GAC AAG TCC TAT AGA TGC GTC TTA CAA CAA GAA         1064
His Lys Gly Ala Asp Asp Lys Ser Tyr Arg Cys Val Leu Gln Gln Glu
330                 335                 340

GAT GAA AAT AAC AAG GTA GGT GTT GCC TTA TCC AAG GAT CTG ATG GCA     1112
Asp Glu Asn Asn Lys Val Gly Val Ala Leu Ser Lys Asp Leu Met Ala
        345                 350                 355
```

FIG. 2D

```
GTT GCC GGT GAA GCC CTA AAG GCC AAC ATC ACG ACC CTT GGT CCC CTC    1160
Val Ala Gly Glu Ala Leu Lys Ala Asn Ile Thr Thr Leu Gly Pro Leu
360                 365                 370

GTG CTC CCC ATG TCA GAA CAA CTC CTC TTC TTT GCC ACC TTA GTG GCA    1208
Val Leu Pro Met Ser Glu Gln Leu Leu Phe Phe Ala Thr Leu Val Ala
375                 380                 385                 390

CGT AAG GTC TTC AAG ATG ACG AAC GTG AAG CCA TAC ATC CCA GAT TTC    1256
Arg Lys Val Phe Lys Met Thr Asn Val Lys Pro Tyr Ile Pro Asp Phe
        395                 400                 405

AAG TTG GCA GCG AAC GAC TTC TGC ATC CAT GCA GGA GGC AAA GCA GTG    1304
Lys Leu Ala Ala Asn Asp Phe Cys Ile His Ala Gly Gly Lys Ala Val
410                 415                 420

TTG GAT GAG CTC GAG AAG TTG AAC TTG GAG TTG ACG CCA TGG CAC CTT GAA    1352
Leu Asp Glu Leu Glu Lys Leu Asn Leu Glu Leu Thr Pro Trp His Leu Glu
425                 430                 435

CCC TCG AGG ATG ACA CTG TAT AGG TTT GGG AAC ACA TCG AGT AGC TCA    1400
Pro Ser Arg Met Thr Leu Tyr Arg Phe Gly Asn Thr Ser Ser Ser Ser
440                 445                 450
```

FIG. 2E

```
TTA TGG TAC GAG TTG GCA TAC GCT GAA GCA AAA GGG AGG ATC CGT AAG  1448
Leu Trp Tyr Glu Leu Ala Tyr Ala Glu Ala Lys Gly Arg Ile Arg Lys
455                     460                 465                 470

GGT GAT CGA ACT TGG ATG ATT GGA TTT GGT TCA GGT TTC AAG TGT AAC  1496
Gly Asp Arg Thr Trp Met Ile Gly Phe Gly Ser Gly Phe Lys Cys Asn
        475                 480                 485

AGT GTT GTG TGG AGG GCT TTG AGG AGT GTC AAT CCG GCT AGA GAG AAG  1544
Ser Val Val Trp Arg Ala Leu Arg Ser Val Asn Pro Ala Arg Glu Lys
        490                 495                 500

AAT CCT TGG ATG GAT GAA ATT GAG AAG TTC CCT GTC CAT GTG CCT AAA  1592
Asn Pro Trp Met Asp Glu Ile Glu Lys Phe Pro Val His Val Pro Lys
505                 510                 515

ATC GCA CCT ATC GCT TCG TAGAACTGCT AGGATGTGAT TAGTAATGAA        1640
Ile Ala Pro Ile Ala Ser
520

AAATGTGTAT TATGTTAGTG ATGTAGAAAA AGAAACTTTA GTTGATGGGT GAGAACATGT 1700

CTCATTGAGA ATAACGTGTG CATCGTTGTG TTG                            1733
```

FIG. 2F

```
GTCGACACA ATG AAG GCC AAA ACA ATC ACA AAC CCG GAG ATC CAA GTC TCC    51
          Met Lys Ala Lys Thr Ile Thr Asn Pro Glu Ile Gln Val Ser
            1                   5                  10

ACG ACC ATG ACC ACC ACG ACC GCC ACT CTC CCC AAC TTC AAG              99
Thr Thr Met Thr Thr Thr Thr Ala Thr Leu Pro Asn Phe Lys
 15                  20                  25              30

TCC ATC AAC TTA CAC CAC GTC AAG CTC GGC TAC CAC TAC TTA ATC         147
Ser Ile Asn Leu His His Val Lys Leu Gly Tyr His Tyr Leu Ile
         35                  40                  45

TCC AAT GCC CTC TTC CTC GTA TTC ATC CCC CTT TTG GGC CTC GCT TCG     195
Ser Asn Ala Leu Phe Leu Val Phe Ile Pro Leu Leu Gly Leu Ala Ser
         50                  55                  60

GCC CAC CTC TCC TCC TTC TCG GCC CAT GAC TTG TCC CTG CTC TTC GAC     243
Ala His Leu Ser Ser Phe Ser Ala His Asp Leu Ser Leu Leu Phe Asp
         65                  70                  75

CTC CTT CGC CGC AAC CTC CCC GTT GTC GTT TGT TCT TTC CTC TTC         291
Leu Leu Arg Arg Asn Leu Pro Val Val Val Cys Ser Phe Leu Phe
         80                  85                  90

FIG. 3A
```

```
GTT TTA TTA GCA ACC CTA CAT TTC TTG ACC CGG CCT AGG AAT GTC TAC        339
Val Leu Leu Ala Thr Leu His Phe Leu Thr Arg Pro Arg Asn Val Tyr
 95                     100                 105                 110

TTG GTG GAC TTT GCC TGC TAT AAG CCT CAC CCG AAC CTG ATA ACA TCC        387
Leu Val Asp Phe Ala Cys Tyr Lys Pro His Pro Asn Leu Ile Thr Ser
                    115                 120                 125

CAC GAG ATG TTC ATG GAC CGG ACC TCC CGG GCC GGG TCG TTT TCT AAG        435
His Glu Met Phe Met Asp Arg Thr Ser Arg Ala Gly Ser Phe Ser Lys
                    130                 135                 140

GAG AAT ATT GAG TTT CAG AGG AAG ATC TTG GAG AGG GCC GGT ATG GGC        483
Glu Asn Ile Glu Phe Gln Arg Lys Ile Leu Glu Arg Ala Gly Met Gly
                    145                 150                 155

CGG GAA ACC TAC GTC CCC GAA TCC GTC ACT AAG GTG CCG CCC GAG CCG        531
Arg Glu Thr Tyr Val Pro Glu Ser Val Thr Lys Val Pro Pro Glu Pro
160                 165                 170

AGC ATA GCA GCC AGG GCC GAG GCG GAG GAG GTG ATG TAC GGG GCG            579
Ser Ile Ala Ala Arg Ala Glu Ala Glu Glu Val Met Tyr Gly Ala
175                 180                 185                 190
```

FIG. 3B

```
ATC GAC GAG GTG TTG GAG AAG ACG GGG GTG AAG CCG AAG CAG ATA GGA    627
Ile Asp Glu Val Leu Glu Lys Thr Gly Val Lys Pro Lys Gln Ile Gly
                195                 200                 205

ATA CTG GTG GTG AAC TGC AGC TTG TTT AAC CCA ACG CCG TCG CTG TCA    675
Ile Leu Val Val Asn Cys Ser Leu Phe Asn Pro Thr Pro Ser Leu Ser
            210                 215                 220

TCC ATG ATA GTT AAC CAT TAC AAG CTT AGG GGT AAT ATA CTT AGC TAT    723
Ser Met Ile Val Asn His Tyr Lys Leu Arg Gly Asn Ile Leu Ser Tyr
        225                 230                 235

AAT CTT GGT TGC ATG GGT TGC AGT GCT GGG CTC ATT TCC ATT GAT CTT    771
Asn Leu Gly Cys Met Gly Cys Ser Ala Gly Leu Ile Ser Ile Asp Leu
    240                 245                 250

GCC AAG GAC CTC CTA CAG GTT TAC CGT AAC ACA TAT GTG TTA GTA GTG    819
Ala Lys Asp Leu Leu Gln Val Tyr Arg Asn Thr Tyr Val Leu Val Val
255                 260                 265                 270

AGC ACA GAA AAC ATG ACC CTT AAT TGG TAC TGG TAT GGC AAT GAC CGC TCC    867
Ser Thr Glu Asn Met Thr Leu Asn Trp Tyr Trp Tyr Gly Asn Asp Arg Ser
            275                 280                 285
```

FIG. 3C

```
ATG CTT ATC ACC AAC TGC CTA TTT CGC ATG GGT GCT ATC ATC   915
Met Leu Ile Thr Asn Cys Leu Phe Arg Met Gly Ala Ile Ile
        290                 295                 300

CTC TCA AAC CGC TGG CGT GAT CGT CGA TCC AAG TAC CAA CTC CTT   963
Leu Ser Asn Arg Trp Arg Asp Arg Arg Ser Lys Tyr Gln Leu Leu
            305                 310                 315

CAC ACA GTA CGC ACC CAC AAG GGC GAC GAC AAG TCC TAT AGA TGC  1011
His Thr Val Arg Thr His Lys Gly Asp Asp Lys Ser Tyr Arg Cys
320                 325                 330

GTC TTA CAA CAA GAA GAT GAA AAT AAC AAG GTA GGT GTT GCC TTA TCC  1059
Val Leu Gln Gln Glu Asp Glu Asn Asn Lys Val Gly Val Ala Leu Ser
    335                 340                 345                 350

AAG GAT CTG ATG GCA GTT GCC GGT GAA GCC CTA AAG GCC AAC ATC ACG  1107
Lys Asp Leu Met Ala Val Ala Gly Glu Ala Leu Lys Ala Asn Ile Thr
                355                 360                 365

ACC CTT GGT CCC CTC GTG CTC CCC ATG TCA GAA CAA CTC CTC TTC TTT  1155
Thr Leu Gly Pro Leu Val Leu Pro Met Ser Glu Gln Leu Leu Phe Phe
        370                 375                 380
```

FIG. 3D

```
GCC ACC TTA GTG GCA CGT AAG GTC TTC AAG ATG ACG AAC GTG AAG CCA    1203
Ala Thr Leu Val Ala Arg Lys Val Phe Lys Met Thr Asn Val Lys Pro
        385                 390                 395

TAC ATC CCA GAT TTC AAG TTG GCA GCG AAG CAC TTC TGC ATC CAT GCA    1251
Tyr Ile Pro Asp Phe Lys Leu Ala Ala Lys His Phe Cys Ile His Ala
        400                 405                 410

GGA GGC AAA GCA GTG TTG GAT GAG CTC GAG ACG AAC TTG GAG TTG ACG    1299
Gly Gly Lys Ala Val Leu Asp Glu Leu Glu Thr Asn Leu Glu Leu Thr
        415                 420                 425             430

CCA TGG CAC CTT GAA CCC TCG AGG ATG ACA CTG TAT AGG TTT GGG AAC    1347
Pro Trp His Leu Glu Pro Ser Arg Met Thr Leu Tyr Arg Phe Gly Asn
        435                 440                 445

ACA TCG AGT AGC TCA TTA TGG TAC GAG TTG GCA TAC GCT GAA GCA AAA    1395
Thr Ser Ser Ser Ser Leu Trp Tyr Glu Leu Ala Tyr Ala Glu Ala Lys
        450                 455                 460

GGG AGG ATC CGT AAG GGT GAT CGA ACT TGG ATG ATT GGA TTT GGT TCA    1443
Gly Arg Ile Arg Lys Gly Asp Arg Thr Trp Met Ile Gly Phe Gly Ser
        465                 470                 475
```

FIG. 3E

```
GGT TTC AAG TGT AAC AGT GTT GTG TGG AGG GCT TTG AGG AGT GTC AAT   1491
Gly Phe Lys Cys Asn Ser Val Val Trp Arg Ala Leu Arg Ser Val Asn
        480                 485                 490

CCG GCT AGA GAG AAG AAT CCT TGG ATG GAT GAA ATT GAG AAT TTC CCT   1539
Pro Ala Arg Glu Lys Asn Pro Trp Met Asp Glu Ile Glu Asn Phe Pro
495                 500                 505                 510

GTC CAT GTG CCT AAA ATC GCA CCT ATC GCT TCG TAGAACTGCT AGGATGTGAT 1592
Val His Val Pro Lys Ile Ala Pro Ile Ala Ser
                515                 520

TAGTAATGAA AAATGTGTAT TATGTTAGTG ATGTAGAAAA AGAAACTTTA GTTGATGGGT 1652

GAGAACATGT CTCATTGAGA ATAACGTGTG CATCGTTGTG TTGAATTTGA ATTTGAGTAT 1712

TGGTGAAATT CTGTTAGAAT TGACGCATGA GTCATATATA TACAAATTTA AGTAAGATTT 1772

TACGCTTTCT T                                                      1783
```

FIG. 3F

```
GGCGCGCCGG  TACCTCTAGA  CCTGGCGATT  CAACGTGGTC  GGATCATGAC  GCTTCCAGAA    60

AACATCGAGC  AAGCTCTCAA  AGCTGACCTC  TTTCGGATCG  TACTGAACCC  GAACAATCTC   120

GTTATGTCCC  GTCGTCTCCG  AACAGACATC  CTCGTAGCTC  GGATTATCGA  CGAATCCATG   180

GCTATACCCA  ACCTCCGTCT  TCGTCACGCC  TGGAACCCTC  TGGTACGCCA  ATTCCGCTCC   240

CCAGAAGCAA  CCGGCGCCGA  ATTGCGCGAA  TTGCTGACCT  GGAGACGGAA  CATCGTCGTC   300

GGGTCCTTGC  GCGATTGCGG  CGGAAGCCGG  GTCGGGTTGG  GGACGAGACC  CGAATCCGAG   360

CCTGGTGAAG  AGTTGTTCA   TCGGAGATTT  ATAGACGGAG  ATGGATCGAG  CGGTTTTGGG   420

GAAAGGGGAA  GTGGGTTTGG  CTCTTTTGGA  TAGAGAGAGT  GCAGCTTTGG  AGAGAGACTG   480

GAGAGGTTTA  GAGAGAGACG  CGGCGGATAT  TACCCGGAGGA GAGGCGACGA  GAGATAGCAT   540

TATCGAAGGG  GAGGGAGAAA  GAGTGACGTG  GAGAAATAAG  AAACCGTTAA  GAGTCGGATA   600
```

FIG. 4A

```
TTTATCATAT TAAAAGCCCA ATGGGCCTGA ACCCATTTAA ACAAGACAGA TAAATGGGCC    660
GTGTGTTAAG TTAACAGAGT GTTAACGTTC GGTTTCAAAT GCCAACGCCA TAGGAACAAA    720
ACAAACGTGT CCTCAAGTAA ACCCCTGCCG TTTACACCTC AATGGCTGCA TGGTGAAGCC    780
ATTAAACACG TGGCGTAGGAT GCATGACGAC GCCATTGACA CCTGACTCTC TTCCCTTCTC    840
TTCATATATC TCTAATCAAT TCAACTACTC ATTGTCATAG CTATTCGGAA AATACATACA    900
CATCCTTTTC TCTTCGATCT CTCTCAATTC ACAAGAAGCA AAGTCGACGG ATCCCTGCAG    960
TAAATTACGC CATGACTATT TTCATAGTCC AATAAGGCTG ATGTCGGGAG TCCAGTTTAT   1020
GAGCAATAAG GTGTTTAGAA TTTGATCAAT GTTTATAATA AAAGGGGGAA GATGATATCA   1080
CAGTCTTTTG TTCTTTTTGG CTTTTGTTAA ATTTGTGTGT TTCTATTTGT AAACCTCCTG   1140
TATATGTTGT ACTTCTTTCC CTTTTTAAGT GGTATCGTCT ATATGGTAAA ACGTTATGTT   1200
```

FIG. 4B

```
TGGTCTTTCC TTTTCTCTGT TTAGGATAAA AAGACTGCAT GTTTTATCTT TAGTTATATT 1260

ATGTTGAGTA AATGAACTTT CATAGATCTG GTTCCGTAGA GTAGACTAGC AGCCGAGCTG 1320

AGCTGAACTG AACAGCTGGC AATGTGAACA CTGGATGCAA GATCAGATGT GAAGATCTCT 1380

AATATGGTGG TGGGATTGAA CATATCGTGT CTATATTTTT GTTGGCATTA AGCTCTTAAC 1440

ATAGATATAA CTGATGCAGT CATTGGTTCA TACACATATA TAGTAAGGAA TTACAATGGC 1500

AACCCAAAACT TCAAAAACAG TAGGCCACCT GAATTGCCTT ATCGAATAAG AGTTTGTTTC 1560

CCCCCACTTC ATGGGATGTA ATACATGGGA TTTGGGAGTT TGAATGAACG TTGAGACATG 1620

GCAGAACCTC TAGAGGTACC GGCGCGC                                    1647
```

FIG. 4C

JOJOBA WAX BIOSYNTHESIS GENE

This application is a continuation-in-part of U.S. Ser. No. 07/796,256 filed Nov. 20, 1991, now abandoned, and a continuation-in-part of U.S. Ser. No. 07/933,411 filed Aug. 21, 1992, now abandoned, and a continuation-in-part of PCT/US92/09863 filed Nov. 13, 1992.

TECHNICAL FIELD

The present invention is directed to enzymes, methods to purify, and obtain such enzymes, amino acid and nucleic acid sequences related thereto, and methods of use for such compositions in genetic engineering applications.

INTRODUCTION

Background

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

A desirable goal which involves such genetic engineering techniques, is the ability to provide crop plants having a convenient source of wax esters. Wax esters are required in a variety of industrial applications, including pharmaceuticals, cosmetics, detergents, plastics, and lubricants. Such products, especially long chain wax esters have previously been available from the sperm whale, an endangered species, or more recently, from the desert shrub, jojoba. Neither of these sources provides a convenient supply of wax esters. Thus, in order to obtain a reliable source of such compounds, transformation of crop plants, which are easily manipulated in terms of growth, harvest and extraction of products, is desirable.

In order to obtain such transformed plants, however, the genes responsible for the biosynthesis of the desired wax ester products must first be obtained. Wax ester production results from the action of at least two enzymatic activities, fatty acyl reductase and fatty acyl:fatty alcohol acyltransferase, or wax synthase. Preliminary studies with such enzymes and extensive analysis and purification of a fatty acyl reductase, indicate that these proteins are associated with membranes, however the enzyme responsible for the fatty acyl:fatty alcohol ligation reaction in wax biosynthesis has not been well characterized. Thus, further study and ultimately, purification of this enzyme is needed so that the gene sequences which encode the enzymatic activity may be obtained.

It is desirable, therefore, to devise a purification protocol whereby the wax synthase protein may be obtained and the amino acid sequence determined and/or antibodies specific for the wax synthase obtained. In this manner, library screening, polymerase chain reaction (PCR) or immunological techniques may be used to identify clones expressing a wax synthase protein. Clones obtained in this manner can be analyzed so that the nucleic acid sequences corresponding to wax synthase activity are identified. The wax synthase nucleic acid sequences may then be utilized in conjunction with fatty acyl reductase proteins, either native to the transgenic host cells or supplied by recombinant techniques, for production of wax esters in host cells.

Relevant Literature

Cell-free homogenates from developing jojoba embryos were reported to have acyl-CoA fatty alcohol acyl transferase activity. The activity was associated with a floating wax pad which formed upon differential centrifugation (Pollard et al. (1979) supra; Wu et al. (1981) supra).

Solubilization of a multienzyme complex from *Euglena gracilis* having fatty acyl-SCoA transacylase activity is reported by Wildner and Hallick (Abstract from *The Southwest Consortium Fifth Annual Meeting*, Apr. 22–24, 1990, Las Cruces, N. Mex.).

Ten-fold purification of jojoba acyl-CoA: alcohol transacylase protein is reported by Pushnik et al. (Abstract from *The Southwest Consortium Fourth Annual Meeting*, Feb. 7, 1989, Riverside, Calif.).

An assay for jojoba acyl-CoA:alcohol transacylase activity was reported by Garver et al. (*Analytical Biochemistry* (1992) 207:335–340).

BRIEF DESCRIPTION OF THE DRAWINGS

FIGS. 1A–1F. The nucleic acid sequence and translated amino acid sequence of a jojoba fatty acyl reductase (SEQ ID NO: 9), as determined from the cDNA sequence, is provided in FIG. 1.

FIGS. 2A–2F. Preliminary nucleic acid sequence and translated amino acid sequence (SEQ ID NO: 10) of a jojoba cDNA clone are provided.

FIGS. 3A–3F. Nucleic acid and translated amino acid sequences of second class of jojoba clones (SEQ ID NO: 11), as represented by the sequence of pCGN7614, is provided.

FIGS. 4A–4C. Nucleic acid sequence of an oleosin expression cassette is provided (SEQ ID NO: 12).

SUMMARY OF THE INVENTION

By this invention, a partially purified fatty acyl-CoA: fatty alcohol O-acyltransferase protein, is provided, wherein said protein is active in the formation of wax esters from fatty alcohol and fatty acyl substrates. This fatty acyl-CoA: fatty alcohol O-acyltransferase is also referred to herein as "wax synthase". The wax synthase of this invention may be active with a variety of fatty acyl and fatty alcohol substrates, including acyl-CoAs and acyl-ACPs. The carbon chain length of these substrates may vary, although a given wax synthase may show preference for acyl and alcohol substrates having a specific chain length or may be active with acyl and alcohol substrates having a wide range with respect to carbon chain length.

In general, the wax synthase of this invention has activity towards at least those acyl and alcohol substrates having a chain length of from 12 to 24 carbons, which carbon chain length may be represented by the formula "$C_{2x}$", where "x" is a number from 6 to 12, although other acyl or alcohol substrates may be tested and further activities discovered. In addition, having obtained the wax synthase protein of this invention, further manipulations are now possible as described in further detail below. These manipulations may lead to production or discovery of other related wax synthases.

Thus, in a first aspect, this invention relates to protein preparations demonstrating wax synthase enzymatic activity, and is exemplified by a seed-plant protein preparation. Such a preparation is produced by fractionation of jojoba embryos to produce a microsomal membrane preparation, solubilization of the wax synthase protein from this membrane preparation and further purification by chromatographic procedures. The jojoba wax synthase is shown herein to accept a broad range of acyl and alcohol substrates, which may be saturated or unsaturated (containing one or more double bonds between carbons). The activity of the jojoba wax synthase enzyme is given as E.C.2.3.1.75 in Enzyme Nomenclature 1984, with the recommended name "long-chain alcohol fatty-acyl transferase".

By these procedures, a partially purified protein preparation is obtained which contains a wax synthase protein having an apparent molecular mass of approximately 57 kD. Thus, methods of obtaining wax synthase proteins through purification from seed-plant sources are provided, as well as methods to obtain amino acid sequences of these wax synthase proteins.

In addition, wax synthase proteins from other organisms are provided by methods described herein. For example, a partially purified preparation of an Acinetobacter wax synthase is obtained, wherein the wax synthase activity is discovered to be associated with an approximately 45 kD peptide band. Similarly, a wax synthase protein preparation from *Euglena gracilis* is provided, wherein a 41 kD peptide is associated with wax synthase activity.

In a different aspect of this invention, nucleic acid sequences associated with a wax synthase of this invention are considered. Methods are described whereby these sequences may be identified and obtained from the amino acid sequences of the wax synthase proteins of this invention. Uses of the structural gene sequences for isolation of other wax synthase sequences, as well as in recombinant constructs for transcription of wax synthase nucleic acid sequences and/or expression of wax synthase proteins in host cells are described. Uses of other nucleic acid sequences associated with wax synthase protein are also considered, such as the use of 5' and 3' noncoding regions.

In yet a different aspect of this invention, cells containing recombinant constructs coding for sense and antisense wax synthase sequences are considered. In particular, cells which contain the preferred acyl-CoA substrates of a jojoba wax synthase, such as those cells in embryos of Brassica plants, are considered.

In addition, cells containing the wax synthase protein of this invention as the result of expression from the recombinant constructs of this invention are considered, and a method of producing a wax synthase in a host cell is provided. Accordingly, a wax synthase protein that is recovered as the result of expression of that protein in a host cell is also considered in this invention.

Further, it may be recognized that the wax synthases of this invention may find application in the production of wax esters in such host cells which contain fatty acyl and fatty alcohol substrates of the wax synthase. Such host cells may exist in nature or be obtained by transformation with nucleic acid constructs which encode a fatty acyl reductase. Fatty acyl reductase, or "reductase", is active in catalyzing the reduction of a fatty acyl group to the corresponding alcohol. Co-pending U.S. patent applications 07/659,975 (filed Feb. 22, 1991), 0767,251 (filed Sep. 27, 1991) and 07/920,430 (filed Jul. 31, 1992), which are hereby incorporated by reference, are directed to such reductase proteins. This information is also provided in published PCT patent application WO 92/14816. In addition, other sources of wax synthase proteins are described herein which are also desirable sources of reductase proteins.

Especially considered in this aspect of the invention, are plant cells which contain the preferred alcohol substrates of a jojoba wax synthase described herein. A method of providing plant cells with such alcohol substrates is considered wherein said cells are transformed with recombinant nucleic acid constructs which encode a fatty acyl reductase nucleic acid sequence. Thus, plant hosts which do not normally contain significant amounts of the alcohol substrates utilized by wax synthase, may be transformed with a reductase construct such that the alcohols are produced. In this manner, the fatty acyl groups present in the host cell will also provide the source of fatty alcohol substrate utilized by wax synthase in the synthesis of wax esters. Depending on the specificities of the wax synthase and reductase proteins, one recognizes that in this manner, plant cells may be obtained which produce a variety of desirable wax ester products. Such products will have different properties depending on the chain length and degree of saturation of the fatty alcohol and fatty acyl groups. Thus, the wax ester products produced according to the methods herein may be recovered from the host cells and are also considered in this invention.

DETAILED DESCRIPTION OF THE INVENTION

A fatty acyl-CoA: fatty alcohol acyltransferase of this invention includes any sequence of amino acids, such as protein, polypeptide or peptide fragment, which is active in catalyzing the esterification of a fatty alcohol by a fatty acyl group to produce a wax ester. The acyl-CoA: alcohol acyltransferase of this invention is also referred to hereafter as "wax synthase".

Although typically referred to as an acyl-CoA: alcohol acyltransferase, the wax synthases of this invention may demonstrate activity towards a variety of acyl substrates, including fatty acyl-CoA and fatty acyl-ACP molecules. In addition, both the acyl and alcohol substrates acted upon by the wax synthase may have varying carbon chain lengths and degrees of saturation, although the wax synthase may demonstrate preferential activity towards certain molecules.

Many different organisms produce wax esters from alcohol and acyl substrates and are desirable sources of a wax synthase protein of this invention. For example, plants produce epidermal, or cuticular wax (Kolattukudy (1980) in *The Biochemistry of Plants* (Stumpf, P. K. and Conn, E. E., eds.) Vol.4, p. 571-645), and the desert shrub, jojoba, produces a seed storage wax (Ohlrogge et al. (*Lipids* (1978) 13:203-210). Wax synthesis has also been observed in various species of bacteria, such as Acinetobacter (Fixter et al. (1986) *J. Gen. Microbiol.* 132:3147-3157) and *Micrococcus* (Lloyd (1987) *Microbios* 52:29-37), and by the unicellular orgnanism, Euglena (Khan and Kolattukudy (1975) *Arch. Biochem. Biophys.* 170:400-408). In addition, wax production and wax synthase activity have been reported in microsomal preparations from bovine meibomian glands (Kolattukudy et al. (1986) *J. Lipid Res.* 27:404–411), avian uropygial glands, and various insect and marine organisms. Consequently, many different wax esters which will have various properties may be produced by the wax synthases of this invention, and the activity of the enzyme and type of wax ester produced may depend upon the available substrate or the substrate specificity of the particular wax synthase of interest.

To obtain a reliable source of a wax synthase protein for use in esterification reactions, it is desirable to isolate nucleic acid sequences associated with the wax synthase such that these sequences may be cloned into host cells for the production of the wax synthase enzyme. For example, one may clone nucleic acid sequences encoding a wax synthase protein into vectors for expression in *E. coli* cells to provide a ready source of the wax synthase protein. The wax synthase protein so produced may also be used to raise antibodies against wax synthase proteins for use in identification and purification of related wax synthase proteins from various sources, especially from plants. In addition, further study of the wax synthase protein may lead to site-specific mutagenesis reactions to further characterize and improve its catalytic properties or to alter its fatty alcohol or fatty acyl substrate specificity. A wax synthase with altered substrate specificity may find application in conjunction with other FAS enzymes.

Prior to the instant invention, amino acid sequences of wax synthase proteins were not known. Thus, in order to obtain the nucleic acid sequences associated with wax synthase, it was necessary to first purify the protein from an available source and determine at least partial amino acid sequence so that appropriate probes useful for isolation of wax synthase nucleic acid sequences could be prepared.

The desert shrub, *Simmondsia chinensis* (jojoba) was identified as a source of a candidate wax synthase protein. Initial studies reveal that the jojoba wax synthase is an integral membrane protein and hydrophobic in nature. In general, membrane associated proteins are difficult to purify as they tend to lose enzymatic activity when they are solubilized, i.e. separated from the membrane environment in which they normally function. Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized membrane protein, a microsomal membrane preparation which comprises wax synthase activity is desired. Standard microsomal membrane preparations utilize differential centrifugation of a cell-free homogenate (CFH) to yield a membrane fraction which is free of whole cells, nuclei and soluble protein. (See, for example Moore et al. (1987) *Biological Membranes: A Practical Approach*, pp. 37–72, eds. Finalay and Evans.) With oilseeds, initial centrifugation steps typically yield a pellet, supernatant and a floating fat pad, and microsomal membranes may then be recovered by further centrifugation of the supernatant.

A protocol is described in co-pending U.S. Ser. No. 07/659,975, filed Feb. 22, 1991, whereby a jojoba membrane fraction was obtained with good recovery of enzyme activity associated with fatty acyl reductase, another enzyme involved in the formation of wax esters in jojoba. The method also provides membrane fractions having wax synthase activity as described in detail in the examples which follow. Other procedures are known to those in the art and may be utilized to obtain similar membrane preparations. In addition, methods to assay for wax synthase activity in such preparations are described in Example 1.

A critical stage for further enzyme characterization and purification is that of obtaining solubilized wax synthase protein that is separated from its native lipid bilayer membrane environment, but retains substantial amounts of measurable wax synthase enzymatic activity. The removal of integral membrane proteins from the lipid bilayer is typically accomplished using amphiphilic detergents in aqueous solution, although organic solvents have also been used in a few cases. Many different detergents and methods of solubilization of membrane proteins are known to those skilled in the art, and are also reviewed by Neugebauer (*Methods Enzymol.* (1990) 182:239–253) and Hjelmiland (*Methods Enzymol.* (1990) 182:253–264).

Often, detergents which are used to solubilize membrane proteins are found to inhibit the enzymatic activity of a desired protein. Several detergents were tested for solubilization of jojoba wax synthase, including CHAPS (3-[(3-cholamidopropyl)-dimethyl-ammonio]-1-propanesulfonate), which was demonstrated in copending U.S. Ser. No. 07/659,975, to be useful in purification of a fatty acyl reductase from jojoba. All were found to inhibit wax synthase enzymatic activity. Although strong inhibition by CHAPS was observed at concentrations above the CMC, it was found that addition of phospholipids, such as L-phosphatidyl choline, and adjustment of the CHAPS concentration from 0.75% to 0.3%, i.e. to below the CMC, results in reconstitution of a portion of the wax synthase activity. The primary requirement for reconstitution of wax synthase activity is the presence of phospholipids during the removal or dilution of the detergent, so that the wax synthase protein is incorporated into phospholipid vesicles. This differs from the protocol developed for reconstitution of jojoba reductase activity, which does not require addition of phospholipids. Thus, if phospholipids are present in a wax synthase preparation, such as that from a microsomal membrane fraction, activity may be detected simply by removal or dilution of detergent. However, in further purified wax synthase preparations, phospholipids must be added to detect activity. If high levels, ie. greater than approximately 2% (w/v) of phospholipids are used, wax synthase activity may be restored by simple dilution of the detergent used for solubilization. A method to reconstitute and assay wax synthase activity in solubilized wax synthase preparations is described in Example 1.

A protocol for solubilizing jojoba wax synthase activity utilizing the detergent CHAPS is described in Example 4. Yields of approximately 15% of the wax synthase activity from the microsomal membrane preparation are obtained. Similarly, studies of reversibility of apparent wax synthase inhibition by other detergents may be conducted to identify other useful detergents for solubilization of the jojoba or other candidate wax synthases. As the percentage of wax synthase activity which is solubilized from the microsomal membrane preparation is small, techniques may be developed to increase the percentage of wax synthase obtained in a solubilized form. However, the proportion of solubilized wax synthase obtained by the described methods is sufficient to permit further purification, characterization and sequencing of the wax synthase as described below.

Having obtained solubilized wax synthase protein, it can be seen that further experiments to characterize the enzyme as to substrate specificity, cofactor requirements and possible activity inhibiting agents may now be conducted. For example, it has been found that the jojoba wax synthase of this invention has a broad range of acyl substrates, including acyl-ACP and acyl-CoA molecules. In addition, the acyl and fatty alcohol substrates may have a broad size range with respect to carbon chain length. For example, activity was tested using substrates having carbon chain lengths of from C12 to C24, and all were shown to be utilized by the enzyme. In addition, activity was shown with fatty acyl and fatty alcohols having varying degrees of unsaturation.

A procedure which has proved very useful for further characterization of the wax synthase of this invention is that of specifically labeling the wax synthase protein. For example, it was discovered that membrane preparations having wax synthase activity may be incubated with radiolabeled palmitoyl-CoA, a substrate of the wax synthase enzyme, such that a radiolabeled peptide band of apparent molecular mass of approximately 57 kD is detected by SDS polyacrylamide electrophoresis (PAGE) and subsequent autoradiography. In addition, solubilized wax synthase protein, which no longer demonstrates enzymatic activity, may be similarly labeled to provide a convenient method to track the wax synthase protein through further purification steps. Details of these labeling procedures are described in Example 2.

Thus, preparations comprising wax synthase activity of this invention may be subjected to further techniques, such as SDS polyacrylamide gel electrophoresis (PAGE) and subsequent staining, or radiolabeling with palmitoyl-CoA, followed by SDS PAGE and subsequent autoradiography. In this manner, it is verified that an approximately 57 kD protein is present in these preparations and that the staining intensity of this protein corresponds to levels of wax synthase activity. When palmitoyl-CoA radiolabeling is conducted, SDS PAGE and autoradiography confirm that the labeled band tracks with wax synthase activity. Experiments which verify that the 57 kD peptide band tracks with wax synthase activity in fractions from size exclusion, affinity and reactive dye chromatography, are described in the following examples.

In addition, chromatography techniques may be utilized to provide enriched preparations of plant wax synthase. One such purification step involves chromatography over an immobilized reactive dye matrix, such as the Cibacron Blue F3GA (Blue A) used in this invention. The jojoba wax synthase activity binds to such a column when loaded in a buffer containing approximately 0.4M NaCl, while greater than approximately 85% of other protein passes through or is removed in subsequent washes. As described in copending application U.S. Ser. No. 07/767,251, reductase activity is also bound to the Blue A column under such conditions. It is demonstrated herein that approximately 20% of the wax synthase activity loaded to a Blue A column can be recovered by elution. A small portion of this wax synthase activity is eluted with a 1.0M NaCl buffer wash, which also contains the majority of the reductase activity which is recovered from this column. The majority of the recovered wax synthase activity is obtained by elution with 1.5M NaCl buffer, wash which also contains a small proportion of the reductase activity. Thus, the majority of the recoverable wax synthase activity is separated from the majority of the reductase protein, although the major proteins present in the preparation other than the 57 kD wax synthase, are the 56 and 54 kD reductase proteins.

Further studies of the wax synthase protein following Blue A chromatography indicate that the wax synthase protein may be undergoing aggregation on this column. For example, size exclusion chromatography of Blue A fractions having wax synthase activity on Superose 12 (Pharmacia), results in elution of the majority of wax synthase activity in the void fractions of the column (exclusion limit approximately 5 million daltons), indicating that the wax synthase is in an aggregated form. Importantly, a small fraction (~5%) of the wax synthase activity is detected in the retained fractions, and the size of this peak activity is estimated at ~55 kD by comparison to protein standards. This provides additional evidence that the 57 kD labeled band is wax synthase, and also demonstrates that wax synthase activity is provided by a single polypeptide.

Using such labeling and purification techniques, the jojoba wax synthase protein can be recovered as a substantially purified protein preparation and the amino acid sequence can be obtained. Similarly, due to the hydrophobic nature of the fatty alcohol substrates of wax synthase enzymes, other wax synthases would also be predicted to be associated with membranes in their native cells, and thus purification techniques described herein for jojoba wax synthase, may also be useful in recovery of purified preparation of other wax synthase proteins.

For example, *Euglena gracilis* produces waxes through the enzymatic actions of a fatty acyl-CoA reductase and a fatty acyl-CoA alcohol transacylase, or wax synthase. Typically, waxes having carbon chain lengths ranging from 24–32 are detected in this organism. As described above for jojoba, the Euglena wax synthase enzyme may be solubilized using a CHAPS/NaCl solution, and a partially purified wax synthase preparation is obtained by Blue A chromatography. In this manner, a 41 kD peptide band associated with wax synthase activity is identified.

Acinetobacter species are also known to produce wax ester compositions, although the mechanism is not well defined. As described herein a fatty acyl-CoA alcohol transacylase, or wax synthase activity is detected in Acinetobacter species. The wax synthase activity is solubilized in CHAPS/NaCl, enriched by Blue A column chromatography and may be further purified using such techniques as size exclusion chromatography. By these methods, an approximately 45 kD peptide band associated with wax synthase activity is obtained in a partially purified preparation.

Although the hydrophobic nature of these wax synthase proteins presents challenges to purification, recovery of substantially purified protein can be accomplished using a variety of methods. For example, a preparative electrophoresis apparatus which utilizes continuous elution electrophoresis process, may be used to purify the 57 kD wax synthase protein obtained from the Blue A column. In this manner, gel fractions may be identified which contain the wax synthase protein in a substantially pure form in a liquid solution. The wax synthase protein sample may then be dialyzed, if necessary, and concentrated to provide a convenient protein source for amino acid sequencing techniques.

Alternatively, polyacrylamide gels may be run and the proteins transferred to a membrane support, such as nitrocellulose or polyvinylidenedifluoride (PVDF). The sections of these membranes which contain the wax synthase protein may then be obtained such that the wax synthase is substantially free of other proteins. The wax synthase protein may then be removed from the membranes and further manipulated such that the amino acid sequences is determined. As the wax synthase protein of this invention, transfers poorly to nitrocellulose membranes, PVDF is preferred for sequencing methods.

Thus, amino acid sequence of wax synthase is determined by sequencing N-terminal amino acid regions from whole protein or by preparing fragments of the desired protein by digestion with the chemical cyanogen bromide, or alternatively by enzymatic cleavage using proteases. Examples of proteases which may be useful include trypsin, and endoproteinases lysC, gluC, AspN and argC. The wax synthase peptides obtained in this manner may then be purified and sequenced in accordance with methods familiar to those skilled in the art. These peptide sequences may then be used in gene isolation techniques, including PCR methods and cDNA and genomic library screening.

Further experiments to confirm the identity of the wax synthase may also be desirable, such as expression of the protein in *E. coli*. The wax synthase may then act on fatty acyl and fatty alcohol substrates in such cells to produce wax esters which may be detected by various anlaytical methods. If the host cells do not contain the alcohol substrate of the wax synthase, activity may be verified by assaying cell extracts. Alternatively, wax synthase protein may be prepared by in vitro translation using wax synthase nucleic acid sequences and commercially available translation kits. Addition of microsomal membrane preparations to the in vitro translation sample may be necessary to obtain active wax synthase protein if membrane insertion is critical to activity. Other testing may include immunological assays, whereby antibodies specific for the candidate protein are prepared and found to inhibit wax synthase activity in protein preparations.

Thus, it is desirable to isolate nucleic acid sequences using amino acid sequences determined for the proteins associated with wax synthase activity, both to confirm the identity of an wax synthase protein and to provide for transcription of the sequences and/or expression of the protein in host cells, either prokaryotic or eukaryotic.

As the wax synthase is a membrane bound protein, it may be desirable to express a candidate protein in a plant cell in order to verify the activity. Electroporation or bombardment of plant tissue for transient expression may be useful for this purpose. Ultimately, stable plant expression in a plant which produces substrates recognized by this enzyme is desired. If a plant targeted for transformation with wax synthase sequences does not naturally contain the fatty alcohol and fatty acyl ester substrates of this enzyme, a plant extract may be prepared and assayed for wax synthase activity by adding substrates of the wax synthase to the extract. Constructs and methods for transformation of plant hosts with wax synthase sequences are discussed in more detail below.

The nucleic acids of this invention may be genomic or cDNA and may be isolated from cDNA or genomic libraries or directly from isolated plant DNA. Methods of obtaining gene sequences once a protein is purified and/or amino acid sequence of the protein is obtained are known to those skilled in the art.

For example, antibodies may be raised to the isolated protein and used to screen expression libraries, thus identifying clones which are producing the plant wax synthase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

Wax synthase nucleic acid sequences of this invention include those corresponding to the jojoba wax synthase protein, as well as sequences obtainable from the jojoba protein or nucleic acid sequences. By "corresponding" is meant nucleic acid sequences, either DNA or RNA, including those which encode jojoba wax synthase protein or a portion thereof, regulatory sequences found 5' or 3' to said encoding sequences which direct the transcription or transcription and translation (expression) of the wax synthase in jojoba embryos, intron sequences not present in the cDNA, as well as sequences encoding any leader or signal peptide of a precursor wax synthase protein that may be required for insertion into the endoplasmic reticulum membrane, but is not found in the mature wax synthase enzyme.

By sequences "obtainable" from the jojoba sequence or protein, is intended any nucleic acid sequences associated with a desired wax synthase protein that may be synthesized from the jojoba wax synthase amino acid sequence, or alternatively identified in a different organism, and isolated using as probes jojoba wax synthase nucleic acid sequences or antibodies prepared against the jojoba wax synthase protein. In this manner, it can be seen that sequences of these other wax synthases may similarly be used to isolate nucleic acid sequences associated with wax synthase proteins from additional sources.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual*, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding a wax synthase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding a wax synthase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba wax synthase can be prepared by injecting rabbits or mice (or other appropriate small mammals) with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba wax synthase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (*Focus* (1989) BRL/Life Technologies, Inc. 11:1–5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related wax synthase protein. Other wax synthases may be obtained through the use of the "new" wax synthase in the same manner as the jojoba wax synthase was used.

It will be recognized by one of ordinary skill in the art that wax synthase nucleic acid sequences of this invention may be modified using standard techniques of site specific mutation or PCR, or modification of the sequence may be accomplished in producing a synthetic nucleic acid sequence. These modified sequences are also considered wax synthase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of a wax synthase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the wax synthase protein) may be synthesized using codons preferred by a selected host. Host-preferred codons may be determined, for example, from the codons used most frequently in the proteins expressed in a desired host species.

The nucleic acid sequences associated with wax synthase proteins will find many uses. For example, recombinant constructs can be prepared which can be used as probes or will provide for expression of the wax synthase protein in host cells. Depending upon the intended use, the constructs may contain the sequence which encodes the entire wax synthase, or a portion thereof. For example, critical regions of the wax synthase, such as an active site may be identified. Further constructs containing only a portion of the wax synthase sequence which encodes the amino acids necessary for a desired wax synthase activity may thus be prepared.

Useful systems for expression of the wax synthase sequences of this invention include prokaryotic cells, such as *E. coli*, yeast cells, and plant cells, both vascular and nonvascular plant cells being desired hosts. In this manner, the wax synthase protein may be produced to allow further studies, such as site-specific mutagenesis of encoding sequences to analyze the effects of specific mutations on reactive properties of the wax synthase protein.

The DNA sequence encoding a wax synthase of this invention may be combined with foreign DNA sequences in a variety of ways. By "foreign" DNA sequences is meant any DNA sequence which is not naturally found joined to the wax synthase sequence, including DNA sequences from the same organism which are not naturally found joined to wax synthase sequences. Both sense and antisense constructs utilizing wax synthase encoding sequences are considered, wherein sense sequence may be used for expression of wax synthase in a host cell, and antisense sequences may be used to decrease the endogenous levels of a homologous wax synthase protein naturally produced by a target organism. In addition, the wax synthase gene sequences of this invention may be employed in a foreign host in conjunction with all or part of the sequences normally associated with the wax synthase, such as regulatory or membrane targeting sequences.

In its component parts, a DNA sequence encoding wax synthase is combined in a recombinant construct having, in the 5' to 3' direction of transcription, a transcription initiation control region capable of promoting transcription and translation in a host cell, the nucleic acid sequence encoding wax synthase and a transcription termination region. Depending upon the host, the regulatory regions will vary, and may include regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae,* including genes such as beta-galactosidase, T7 polymerase, tryptophan E and the like.

For the most part, the recombinant constructs will involve regulatory regions functional in plants which provide for expression of the wax synthase gene to produce functional wax synthase protein. The open reading frame, coding for the plant wax synthase or a functional fragment thereof will be joined at its 5' end to a transcription initiation regulatory region such as the wild-type sequence naturally found 5' upstream to the wax synthase structural gene. Numerous other promoter regions from native plant genes are available which provide for a wide variety of constitutive or regulatable, e.g., inducible, expression of structural gene sequences.

In addition to sequences from native plant genes, other sequences can provide for constitutive gene expression in plants, such as regulatory regions associated with Agrobacterium genes, including regions associated with nopaline synthase (Nos), mannopine synthase (Mas), or octopine synthase (Ocs) genes. Also useful are regions which control expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the wax synthase protein is desired in a plant host, the use of all or part of the complete plant wax synthase gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques. Additionally, 5' untranslated regions from highly expressed plant genes may be useful to provide for increased expression of the wax synthase proteins described herein.

The DNA constructs which provide for wax synthase expression in plants may be employed with a wide variety of plant life, particularly, plants which produce the fatty acyl-CoA substrates of the wax synthase enzyme, such as Brassica. Other plants of interest produce desirable fatty acyl substrates, such as medium or long chain fatty acyl molecules, and include but are not limited to rapeseed (Canola varieties), sunflower, safflower, cotton, Cuphea, soybean, peanut, coconut and oil palms, and corn.

As to the fatty alcohol substrate of the wax synthase enzyme, other than jojoba, seed plants are not known to produce large quantities of fatty alcohols, although small amounts of this substrate may be available to the wax synthase enzyme. Therefore, in conjunction with the wax synthase constructs of this invention, it is desirable to provide the target host cell with the capability to produce fatty alcohols from the fatty acyl molecules present in the host cells. For example, a plant fatty acyl reductase and methods to provide for expression of the reductase enzymes in plant cells are described in co-pending application U.S. Ser. No. 07/767,251. The nucleic acid sequence and translated amino acid sequence of the jojoba reductase is provided in FIG. 1. Thus, by providing both the wax synthase and reductase proteins to the host plant cell, wax esters may be produced from the fatty alcohol and fatty acyl substrates.

In addition to the jojoba reductase, reductase enzymes from other organisms may be useful in conjunction with the wax synthases of this invention. Other potential sources of reductase enzymes include Euglena, Acinetobacter, Micrococus, certain insects and marine organisms, and specialized mammalian or avian tissues which are known to contain wax esters, such as bovine meibomian glands or ovian uropygial glands. Other potential sources of reductase proteins may be identified by their ability to produce fatty alcohols or, if wax synthase is also present, wax esters.

The wax synthase and reductase sequences may be provided during the same transformation event, or alternatively, two different transgenic plant lines, one having wax synthase constructs and the other having reductase constructs may be produced by transformation with the various constructs. These plant lines may then be crossed using known plant breeding techniques to provide wax synthase and reductase containing plants for production of wax ester products.

For applications leading to wax ester production, 5' upstream non-coding regions obtained from genes regulated during seed maturation are desired, especially those preferentially expressed in plant embryo tissue, such as regions derived from ACP, oleosin (Lee and Huang (1991) *Plant Physiol.* 96:1395–1397) and napin regulatory regions. Transcription initiation regions which provide for preferential expression in seed tissue, i.e., which are undetectable in other plant parts, are considered desirable for wax ester production in order to minimize any disruptive or adverse effects of the gene product in other plant parts. Further, the seeds of such plants may be harvested and the lipid reserves of these seeds recovered to provide a ready source of wax esters. Thus, a novel seed product may be produced in oilseed plants which, absent transformation with wax synthase constructs as described herein, are not known to produce wax esters as a component of their seed lipid reserves.

Such "seed-specific promoters" may be obtained and used in accordance with the teachings of U.S. Ser. No. 07/147,781, filed Jan. 25, 1988 (now U.S. Ser. No. 07/742,834, filed Aug. 8, 1981), and U.S. Ser. No. 07/494,722 filed on Mar. 16, 1990 having a title "Novel Sequences Preferentially Expressed In Early Seed Development and Methods Related Thereto", all of which copending applications are incorporated herein by reference. In addition, where plant genes, such as the jojoba reductase and wax synthases are expressed, it may be desirable to use the entire plant gene, including 5' and 3' regulatory regions and any introns that are present in the encoding sequence, for expression of the jojoba genes in a transformed plant species, such as Arabidopsis or Brassica.

Regulatory transcription termination regions may be provided in recombinant constructs of this invention as well. Transcription termination regions may be provided by the DNA sequence encoding the plant wax synthase or a convenient transcription termination region derived from a different gene source, especially the transcription termination region which is naturally associated with the transcription initiation region. The transcript termination region will contain at least about 0.5 kb, preferably about 1-3 kb of sequence 3' to the structural gene from which the termination region is derived.

Additional plant gene regions may be used to optimize expression of wax synthase and reductase genes in plant tissues. For example, 5' untranslated regions of highly expressed genes, such as that of the small subunit (SSU) of RuBP-carboxylase, inserted 5' to DNA encoding sequences may provide for enhanced translation efficiency. Portions of the SSU leader protein encoding region (such as that encoding the first 6 amino acids) may also be used in such constructs. In addition, for applications where targetting to plant plastid organelles is desirable, transit peptide encoding sequences from SSU or other nuclear-encoded chloroplast proteins may be used in conjuction with wax synthase and reductase sequences.

Depending on the method for introducing the DNA expression constructs into the host cell, other DNA sequences may be required. Importantly, this invention is applicable to dicotyledyons and monocotyledons species alike and will be readily applicable to new and/or improved transformation and regeneration techniques.

In developing the recombinant construct, the various components of the construct or fragments thereof will normally be inserted into a convenient cloning vector which is capable of replication in a bacterial host, e.g., E. coli. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

In addition to the sequences providing for transcription of wax synthase sequences, the DNA constructs of this invention may also provide for expression of an additional gene or genes, whose protein product may act in conjunction with the wax synthase to produce a valuable end product. For example, as discussed above, DNA constructs which provide for expression of wax synthase and a fatty acyl reductase so that wax esters may produced in transformed hosts, are considered in this invention. Furthermore, production of different wax esters having varying carbon chain lengths and degrees of saturation is desired and may be provided by transforming host plants having fatty alcohol or fatty acyl substrates of varying chain lengths. Such plants may be provided, for example, by methods described in the published international patent application number PCT WO 91/16421, which describes various thioesterase genes and methods of using such genes to produce fatty acyl substrates having varying chain lengths in transformed plant hosts.

Furthermore, to optimize the production of wax esters in oilseed plant hosts, one may wish to decrease the production of the triacylglyceride oils that are normally produced in the seeds of such plants. One method to accomplish this is to antisense a gene critical to this process, but not necessary for the production of wax esters. Such gene targets include diacylglycerol acyltransferase, and other enzymes which catalyse the synthesis of triacylglycerol. Additionally, it may be desirable to provide the oilseed plants with enzymes which may be used to degrade wax esters as a nutrient source, such as may be isolated from jojoba or various other wax producing organisms. In this manner, maximal production of wax esters in seed plant hosts may be achieved.

The wax esters produced in the methods described herein may be harvested using techniques for wax extraction from jojoba or by various production methods used to obtain oil products from various oilseed crops. The waxes thus obtained will find application in many industries, including pharmaceuticals, cosmetics, detergents, plastics, and lubricants. Applications will vary depending on the chain length and degree of saturation of the wax ester components. For example, long chain waxes having a double band in each of the carbon chains are liquid at room temperature, whereas waxes having saturated carbon chain components, may be solid at room temperature, especially if the saturated carbon chains are longer carbon chains.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

When Agrobacterium is utilized for plant transformation, it may be desirable to have the desired nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being permissible so long as a functional complement of the vir genes, which encode transacting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region(s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host *Agrobacterium vir* regions can supply transacting factors required for transfer of the T-DNA bordered sequences to plant host cells. For transformation of Brassica cells, Agrobacterium transformation methods may be used. One such method is described, for example, by Radke et al. (*Theor. Appl. Genet.* (1988) 75:685–694).

The invention now being generally described, it will be more readily understood by reference to the following examples, which are included for purposes of illustration only and are not intended to limit the invention unless so stated.

EXAMPLES

Example 1

Wax Synthase Assays

Methods to assay for wax synthase activity in microsomal membrane preparations or solubilized protein preparations are described.

A. Radiolabeled Material

The substrate generally used in the wax synthase assays, [1-$^{14}$C]palmitoyl-CoA, is purchased from Amersham (Arlington Heights, Ill.). Other chain length substrates were synthesized in order to perform chain length specification studies. Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C]cyanide with the corresponding alcohol mesylate, followed by the base hydrolysis of the alcohol nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10 Ci/mole. [1-$^{14}$C]hexadecanal is prepared by the dichromate oxidation of [1-$^{14}$C]hexadecan-1-ol, according to a micro-scale modification of the method of Pletcher and Tate (*Tet. Lett.* (1978) 1601–1602). The product is purified by preparative silica TLC, and stored as a hexane solution at −70° C. until use.

B. Assay for Wax synthase Activity in a Microsomal Membrane Preparation

Wax synthase activity in a microsomal membrane preparation is measured by incubation of 40 μM [1-$^{14}$C]acyl-CoA (usually palmitoyl-CoA, sp. act. 5.1–5.6 mCi/mmol) and 200 μM oleyl alcohol with the sample to be assayed in a total volume of 0.25 ml. The incubation mixture also contains 20% w/v glycerol, 1 mM DTT, 0.5M NaCl and is buffered with 25 mM HEPES (4-[2-hydroxyethyl]-1-piperazineethane-sulfonic acid). HEPES, here and as referred to hereafter is added from a 1M stock solution adjusted to pH 7.5.

A substrate mixture is prepared in a glass vial, with oleyl alcohol being added immediately before use, and is added to samples. Incubation is carried out at 30° C. for one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Four ml of hexane/isopropanol (3:2, v/v) is added to the terminated assay. The sample is vortexed, 2 ml of aqueous sodium sulphate solution (6.6% w/v) is added, and the sample is again vortexed.

C. Assay for Solubilized Wax Synthase Activity

For assaying solubilized wax synthase activity, reconstitution of the protein is required. Reconstitution is achieved by the addition of phospholipids (Sigam P-3644, ~40% L-phosphatidyl choline) to the 0.75% CHAPS-solubilized sample at a concentration of 2.5 mg/ml, followed by dilution of the detergent to 0.3%, below the CMC. Reconstitution of activity is presumed to be based on the incorporation of wax synthase into the phospholipid vesicles. It is recognized that the amount of wax synthase activity detected after their reconstitution can be influenced by many factors (e.g., the phospholipid to protein ratio and the physical state of the wax synthase protein (e.g. aggregate or dispersed).

D. Analysis of Assay Products

For analyzing the products of either the microsomal membrane preparation wax synthase assay or the solubilized wax synthase assay, two protocols have been developed. One protocol, described below as "extensive assay" is more time-consuming, but yields more highly quantitative results. The other protocol, described below as "quick assay" also provides a measure of wax synthase activity, but is faster, more convenient and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of hexane, and an aliquot is assayed for radioactivity by liquid scintillation counting. The remainder of the sample can be used for TLC analysis of the labeled classes and thereby give a measure of total wax produced.

For lipid class analysis the sample is applied to a silica TLC plate, and the plate is developed in hexane/diethyl ether/acetic acid (80:20:1 v/v/v). The distribution of radioactivity between the lipid classes, largely wax esters, free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis. Reversed-phase TLC systems using C18 plates developed in methanol have also been used for the analysis.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane and spotted on TLC plates and developed and scanned as described for the detailed assay. In this manner the percentage of the total counts which are incorporated into wax is determined.

Example 2

Radiolabeling Wax Synthase Protein

Radiolabeled [1-$^{14}$C]palmitoyl-CoA (Amersham) is added to a wax synthase preparation, either solubilized or a microsomal membrane fraction, in the ratio of 5 μl of label to 40 μl protein sample. The sample is incubated at room temperature for at least 15 minutes prior to further treatment. For SDS-PAGE analysis the sample is treated directly with SDS sample buffer and loaded onto gels for electrophoresis.

Example 3

Further Studies to Characterize Wax Synthase Activity

A. Seed Development and Wax Synthase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Wax synthase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for wax synthase activities as measured in either a cell free homogenate or a membrane fraction, indicate a large induction in activity which peaks at approximately 110–115 days after anthesis. Embryos for enzymology studies were thus harvested between about 90 to 110 days postanthesis, a period when the wax synthase activity is high, lipid deposition has not reached maximum levels, and the seed coat is easily removed. The highest rate of increase of wax synthase activity is seen between days 80 and 90 postanthesis. Embryos for cDNA library construction were thus harvested between about 80 to 90 days postanthesis when presumably the rate of synthase of wax synthase protein would be maximal. Correspondingly, the level of mRNA encoding wax synthase would be presumed to be maximal at this stage.

B. Substrate Specificity

Acyl-CoA and alcohol substrates having varying carbon chain lengths and degrees of unsaturation were added to a microsomal membrane fraction having wax synthase activity to determine the range of substrates recognized by the jojoba wax synthase. Wax synthase activity was measured as described in Example 1, with acyl specificity measured using 80 μM of acyl-CoA substrate and 100 μM of radiolabeled oleyl alcohol. Alcohol specificity was measured using 100 μM of alcohol substrate and 40 μM of radiolabeled eicosenoyl-CoA. Results of these experiments are presented in Table 1 below.

TABLE 1

Acyl and Alcohol Substrate Specificity of Jojoba Wax Synthase

| Substrate Structure | Wax synthase Activity (pmoles/min) | |
|---|---|---|
| | Acyl Group | Alcohol Group |
| 12:0 | 12 | 100 |
| 14:0 | 95 | 145 |
| 16:0 | 81 | 107 |
| 18:0 | 51 | 56 |
| 20:0 | 49 | 21 |
| 22:0 | 46 | 17 |
| 18:1 | 22 | 110 |
| 18:2 | 7 | 123 |
| 20:1 | 122 | 72 |
| 22:1 | 39 | 41 |
| 24:1 | 35 | 24 |

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

C. Effectors of Activity

Various sulphydryl agents were screened for their effect on wax synthase activity. Organomercurial compounds were shown to strongly inhibit activity. Iodoacetamide and N-ethylamaleamide were much less effective. Inhibition by para-hydroxymercuribenzoate was observed, but this inhibition could be reversed by subsequent addition of DTT. These results demonstrate that inhibition by para-hydroxymercuribenzoate involves blocking of an essential sulphydryl group.

D. Size Exclusion Chromatography

A column (1.5 cm×46 cm) is packed with Sephacryl-200 (Pharmacia), sizing range: 5,000–250,000 daltons) and equilibrated with column buffer (25 mM HEPES, 20% glycerol, 0.75% CHAPS, 1 mM EDTA) containing 0.5M NaCl. Approximately 2 ml of a pooled concentrate from a single 1.5M NaCl elution from a Blue A column (see Ex. 4C) is loaded and the column run at 0.5 ml/min. The eluted fractions are assayed for wax synthase activity according to the reconstitution protocol described in Example 1. Wax synthase activity appears as a broad peak beginning at the void fraction and decreasing throughout the remainder of the run. A portion of the fractions having wax synthase activity are treated with 1-$^{14}$C 16:0-CoA (0.0178 uM) for 15 minutes at room temperature. SDS is added to 2% and the samples are loaded on an SDS-PAGE gel. Following electrophoresis, the gel is blotted to Problott (Applied Biosystems; Foster City, Calif.) and the dried blot membrane analyzed by autoradiography. Alternatively, the blot may be scanned for radioactivity using an automated scanning system (AMBIS; San Diego, Calif.). In this manner, it is observed that the 57 kD radiolabeled band tracks with wax synthase activity in the analyzed fractions.

Protein associated with wax synthase activity is further characterized by chromatography on a second size exclusion matrix. A fraction (100 ul) of a 10X concentrated 1.5M NaCl elution from a Blue A column (following a 1.0M NaCl elution step) which contains wax synthase activity is chromatographed on a Superose 12 HR10/30 column (Pharmacia; Piscataway, N.J.) and analyzed by Fast Protein Liquid Chromatography (FPLC) on a column calibrated with molecular weight standards (MW GF-70 and MW GF-1000; Sigma). Activity assays are performed on the eluted fractions. Most 53% of the recovered wax synthase activity is found in the void fractions, but an easily detectable activity is found to elute at ~55 kd according to the calibration curve. These data indicate the minimum size of an active native wax synthase protein is very similar to the 57 kD size of the labeled band, thus providing evidence that wax synthase activity is provided by a single polypeptide. The fraction of wax synthase activity observed in the void fractions is presumably an aggregated form of the enzyme.

E. Palmitoyl-CoA Agarose Chromatography

A column (1.0×3 cm) is packed with 16:0-CoA agarose (Sigma P-5297) and equilibrated with column buffer (See, Example 1, D.) containing 0.2M NaCl. Approximately 4 ml of a pooled concentrate from the 1.5M NaCl wash of the Blue A column is thawed and the salt concentration reduced by passage of the concentrate over a PD-10 (Pharmacia) desalting column equilibrated in 0.2M NaCl column buffer. The reduced salt sample (5 ml) is loaded onto the 16:0 CoA agarose column at a flow rate of 0.15 ml/min. The column is washed with 0.5M NaCl column buffer and then with 1.5M NaCl column buffer. Although some wax synthase activity flows through the column or is removed by the 0.5M NaCl wash, the majority of the recovered activity (21% of the loaded activity) is recovered in the 1.5M NaCl eluted peak.

Portions of the fractions which demonstrate wax synthase activity are radiolabeled with [$^{14}$C]palmitoyl-CoA as described in Example 2 and analyzed by SDS polyacryamide gel electrophoresis (Laemmli, Nature (1970) 227:680–685). Again the approximate 57 kD radio labelled protein band is observed to track with wax synthase activity.

Example 4

Purification of Jojoba Wax Synthase

Methods are described which may be used for isolation of a jojoba membrane preparation having wax synthase activity, solubilization of wax synthase activity and further purification of the wax synthase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 $\mu$g/ml leupeptin, 0.5 $\mu$g/ml pepstatin and 17 $\mu$g/ml PMSF. A cell free homogenate (CFH) is formed by dispersing the powdered embryos in the buffer with a tissue homogenizer (Kinematica, Switzerland; model PT10/35) for approximately 30 sec. and then filtering through three layers of Miracloth (CalBioChem, LaJolla, Calif.). The filtrate is centrifuged at 100,000 x g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 200,000 x g for 1½ hour to yield a pellet, DP2. The pellet is suspended in 25 mM HEPES and 10% glycerol, at 1/20 of the original CFH volume, to yield the microsomal membrane preparation.

Activity is assayed as described in Example 1. Recovery of wax synthase activity is estimated at 34% of the original activity in the cell free homogenate. Wax synthase activity in this preparation is stable when stored at −70° C.

B. Solubilization of Wax synthase Protein

CHAPS (3-[(3-cholamidopropyl)-dimethyl-ammonio]-1-propanesulfonate) and NaCl are added to the microsomal membrane preparation to yield final concentrations of 2% and 0.5M, respectively. The samples are incubated on ice for approximately one hour and then diluted with 25 mM HEPES, 20% glycerol, 0.5M NaCl to lower the CHAPS concentration to 0.75%. The sample is then centrifuged at 200,000 x g for one hour and the supernatant recovered and assayed for wax synthase activity as described in Example 1.C. Typically, 11% of the wax synthase activity from the microsomal membrane preparation is recovered in the supernatant fraction. The solubilized wax synthase activity is stable when stored at −70° C.

C. Blue A Column Chromatography

A column (2.5×8 cm) with a bed volume of approximately 30 ml is prepared which contains Blue A (Cibacron Blue F3GA; Amicon Division, W. R. Grace & Co.), and the column is equilibrated with the column buffer (25 mM HEPES, 20% glycerol, 0.75% CHAPS, 1 mM EDTA) containing 0.4M NaCl. The solubilized wax synthase preparation is diluted to 0.4M NaCl by addition of column buffer (25 mM HEPES, 20% glycerol, 0.75% CHAPS, 1 mM EDTA) and loaded to the Blue A column.

The column is washed with column buffer containing 0.5M NaCl until no protein can be detected (as measured by absorbance at 280 nm) in the buffer flowing through the column. Greater than 94% of the wax synthase activity binds to the column, while greater than 83% of other protein passes through. Typically, approximately 20% of the loaded wax synthase activity is recovered by elution. A portion of the recovered activity (17%) elutes with a 1.0M NaCl column buffer wash, while approximately 75% of the recovered activity elutes as a broad peak in a 150 ml wash with 1.5M NaCl column buffer. Five ml fractions of the 1.5M wash are collected and assayed for wax synthase activity as described in Example 1. Fractions containing wax synthase activity are pooled and concentrated ten fold using an Amicon stirred cell unit and a YM30 membrane. The concentrated wax synthase preparation may be stored at −70° C.

D. SDS PAGE Analysis

Samples from the active BlueA column fractions are diluted in SDS PAGE sample buffer (1x buffer=2% SDS, 30 mM DTT, 0.001% bromphenol blue) and analyzed by electrophoresis on 12% tris/glycine precast gels from NOVEX (San Diego, Calif.). Gels are run at 150 V, constant voltage for approximately 1.5 hours. Protein is detected by silver staining (Blum et al., *Electrophoresis* (1987) 8:93–99). Careful examination of the gel reveals only a few polypeptides, including one of approximately 57 kD, whose staining intensity in the various fractions can be correlated with the amount of wax synthase activity detected in those fractions. Furthermore, if radiolabeled [1-$^{14}$C]palmitoyl-CoA is added to the protein preparation prior to SDS PAGE analysis, autoradiography of the gel reveals that the 57 kD labeled band tracks with wax synthase activity in these fractions. Other proteins are also present in the preparation, including the 56 and 54 kD reductase proteins described in co-pending application U.S. Ser. No. 07/767,251.

E. Continuous Phase Elution

Wax synthase protein is isolated for amino acid sequencing using an SDS-PAGE apparatus, Model 491 Prep Cell (Bio-Rad Laboratories, Inc., Richmond, Calif., according to manufacturer's instructions. A portion (15 ml) of the wax synthase activity from the 1.5M NaCl elution of the Blue A column is concentrated 10 fold in a Centricon 30 (Amicon Division, W. R. Grace & Co.; Beverly, Mass.) and desalted with column buffer on a Pharmacia PD-10 desalting column. The sample is treated with 2% SDS and a small amount of bromphenol blue tracking dye and loaded onto a 5 ml, 4% acrylamide stacking gel over a 20 ml, 12% acrylamide running gel in the Prep Cell apparatus. The sample is electrophoresed at 10 W and protein is continuously collected by the Prep Cell as it elutes from the gel. The eluted protein is then collected in 7.5–10 ml fractions by a fraction collector. One milliliter of each fraction in the area of interest (based on the estimated 57 kD size of the wax synthase protein) is concentrated to 40 μl in a Centricon 30 and treated with 2% SDS. The samples are run on 12% acrylamide mini-gels (Novex) and stained with silver.

Various modifications to the continuous phase elution process in order to optimize for wax synthase recovery may be useful. Such modifications include adjustments of acrylamide percentages in gels volume of the gels, and adjustments to the amount of wax synthase applied to the gels. For example, to isolate greater amounts of the wax synthase protein the Blue A column fractions may be applied to larger volume, 20–50 ml, acrylamide gels at a concentration of approximately 1 mg of protein per 20 ml of gel. The protein fractions eluted from such gels may then be applied 10–15% gradient acrylamide gels for increased band separation.

The protein content of each fraction is evaluated visually and fractions containing wax synthase protein are pooled and concentrated for amino acid sequencing. In order to maximize the amount of wax synthase enzyme collected, fractions which also contain the 56 kD reductase protein band are included in the pooled preparation.

G. Blotting Proteins to Membranes

Alternatively, wax synthase protein may be further isolated for amino acid sequencing by transfer to PVDF membranes following SDS-PAGE, either Immobilon-P (Millipore; Bedford, Mass.) or ProBlott (Applied Biosystems; Foster City, Calif.). Although transfer to nitrocellulose may also be useful, initial studies indicate poor transfer to nitrocellulose membranes, most likely due to the hydrophobic nature of this protein. PVDF membranes, such as ProBlott and Immobilon-P find preferential use in different methods, depending on the amino acid sequencing technique to be employed. For example, transfer to ProBlott is useful for N-terminal sequencing methods and for generation of peptides from cyanogen bromide digestion, Immobilon-P is preferred.

1. Blotting to Nitrocellulose: When protein is electroblotted to nitrocellulose, the blotting time is typically 1–5 hours in a buffer such as 25 mM Tris, 192 mM glycine in 5–20% methanol. Following electroblotting, membranes are stained in 0.1% (w/v) Ponceau S in 1% (v/v) acetic acid for 2 minutes and destained in 2–3 changes of 0.1% (v/v) acetic acid, 2 minutes for each change. These membranes are then stored wet in heat-sealed plastic bags at −20° C. If time permits, blots are not frozen but used immediately for digestion to create peptides for determination of amino acid sequence as described below.

2. Blotting to PYDF: When protein is electroblotted to Immobilon P PVDF, the blotting time is generally about 1–2 hours in a buffer such as 25 mM Tris/192 mM glycine in 20% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below in Example 5A.

Example 5

Determination of Amino Acid Sequence

In this example, methods for determination of amino acid sequences of plant proteins associated with wax synthase activity are described.

A. Cyanogen Bromide Cleavage of Protein and Separation of Peptides

Cyanogen bromide cleavage is performed on the protein of interest using the methodology described in the Probe-Design Peptide Separation System Technical Manual from Promega, Inc. (Madison, Wis.). The wax synthase protein, if not available in a purified liquid sample, is blotted to a PVDF membrane as described above. Purified wax synthase protein or wax synthase bands from the PVDF blot, are placed in a solution of cyanogen bromide in 70% (v/v) formic acid, and incubated overnight at room temperature. Following this incubation the cyanogen bromide solutions are removed, pooled and dried under a continuous nitrogen stream using a Reacti-Vap Evaporator (Pierce, Rockford, Ill.). Additional elution of cyanogen bromide peptides from PVDF may be conducted to ensure complete removal, using a peptide elution solvent such as 70% (v/v) isopropanol, 0.2% (v/v) trifluoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 μl of HPLC grade water is then added to the dried peptides and the water removed by evaporation in a Speed-Vac (Savant, Inc., Farmingdale, N.Y.).

Peptides generated by cyanogen bromide cleavage are separated using a Tris/Tricine SDS-PAGE system similar to that described by Schägger and von Jagow (Anal. Biochem. (1987) 166:368–379). Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3X 2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

B. Protease Digestion and Separation of Peptides

Purified wax synthase protein provided in a liquid solution or wax synthase proteins blotted to nitrocellulose may be subjected to digestion with proteases in order to obtain peptides for sequencing. The method used is that of Aebersold, et al. (PNAS (1987) 85:6970).

For protein provided on nitrocellulose, bands of the wax synthase proteins, and also an equal amount of blank nitrocellulose to be used as a control, are cut out of the nitrocellulose membrane and washed several times with HPLC grade water in order to remove the Ponceau S. Following this wash, 1.0 ml of 0.5% polyvinylpyrrolidone (PVP-40, Aldrich, Milwaukee, Wis.) in 0.5% acetic acid is added to the membrane pieces and this mixture is incubated for 30 minutes at 37° C. In order to remove the PVP-40 completely, nitrocellulose pieces are washed with many volumes of HPLC grade water (8×5 ml), checking the absorbance of the washes at 214 nm on a spectrophotometer. Also, PVP-40 is more easily removed if bands are not cut into small pieces until after PVP-40 treatment and washing.

The proteins, in solution or on nitrocellulose pieces, are then suspended in an appropriate digest buffer, for example trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5–10% (v/v). Proteases are diluted in digest buffer and added to the digest mixture, typically at a ratio of 1:10 (w/w) protease to protein. Digests are incubated 18–24 hours. For example, trypsin digests are incubated at 37° C. and endoproteinase gluC digests are incubated at room temperature. Similarly, other proteases may be used to digest the wax synthase proteins, including lysC and aspN. While the individual digest buffer conditions may be different, the protocols for digestion, peptide separation, purification and sequencing are substantially the same as those described for digestion with trypsin and gluC.

Following overnight incubation, digest reactions are stopped by the addition of 10 μl 10% (v/v) trifluoroacetic acid (TFA) or 1 μl 100% TFA. When the protein is provided on nitrocellulose, the nitrocellulose pieces are washed with 1–5 100 μl volumes of digest buffer with 5–10% acetonitrile, and these volumes are concentrated to a volume of less than 100 μl in a Speed-Vac.

The peptides resulting from digestion are separated on a Vydac reverse phase C18 column (2.1 mm×100 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH 2.2; Buffer B: 70% acetonitrile in 0.1 mM sodium phosphate, pH 2.2. A 3-step gradient of 10–55% buffer B over two hours, 55–75% buffer B over 5 minutes, and 75% buffer B isocratic for 15 minutes at a flow rate of 50 μl/minute is used. Peptides are detected at 214 nm, collected by hand, and then stored at −20° C.

Due to the hydrophobic nature of the wax synthase proteins, addition of a detergent in enzyme digestions buffers may be useful. For example, fractions from the continuous phase elution procedure described above which contain the jojoba wax synthase are concentrated in a Centricon 30 in 100 mM NaHCO$_3$/1.0%

CHAPS to a final volume of 110 μl. Two μg of trypsin in 5 μl of 100 mM Na HCO3/1.0% CHAPS is added to the protein solution and the mixture is incubated overnight at 37° C., and the digestion stopped by addition of trifluoroacetic acid (TFA). The sample is centrifuged lightly and the peptides separated on a Vydac C18 column and eluted as described above. In this procedure, the CHAPS elutes at ~40-53% Buffer B, and obscures the peptide peaks in this region.

Where the primary separation yields a complex peptide pattern, such as where excess protein is used or contaminants (such as the jojoba reductase protein) are present, peptide peaks may be further chromatographed using the same column, but a different gradient system. For the above jojoba wax synthase preparation, hydrophilic peaks were separated using a gradient of 0-40% Buffer B for 60 minutes, 40-75% B for 35 minutes and 75-100% B for 10 minutes. Hydrophobic peaks were separated using 0-40% Buffer B for 40 minutes, 40-80% B for 60 minutes and 80-100% B for 10 minutes. For these separations, Buffer A is 0.1% TFA and Buffer B is 0.1% TFA in acetonitrile.

C. N-terminal Sequencing of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using AC-CESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5-30 pmoles), the 477A conversion cycle and the 120A analyzer as described by Tempst and Riviere (*Anal. Biochem.* (1989) 183:290).

Amino acid seqeunce of jojoba peptides obtained by trypsin digestion as described above are presented in Table 2 below.

TABLE 2

| Amino Acid Sequence of Jojoba Tryptic Peptides | |
| --- | --- |
| SQ1114 | ETYVPESVTKK (SEQ ID NO: 1) |
| SQ1084 | VPXEPSIAAX (SEQ ID NO: 2) |
| SQ1083 | ETYVPEEvtk (SEQ ID NO: 3) |
| SQ1120 | DLMAVAGEAlk (SEQ ID NO: 4) |
| SQ1125 | MTNVKPYIPDF (SEQ ID NO: 5) |
| SQ1129 | FLPXXVAiTGe (SEQ ID NO: 6) |

TABLE 2-continued

| Amino Acid Sequence of Jojoba Tryptic Peptides | |
| --- | --- |
| SQ1131 | FGNTSSXXLyxelayak (SEQ ID NO: 7) |
| SQ1137 | AEAEEVMYGAIDEVLEK (SEQ ID NO: 8) |

The amino acid sequence of peptides is respresented using the one letter code. "X" represents a position where the amino acid could not be identified, and amino acids represented by lower case letters represent residues which were identified with a lesser degree of confidence.

Example 6

Purification of Additional Wax Synthases and Reductases

A. Adaptation of jojoba wax synthase solubilization and purification methods to obtain partially purified preparations of wax synthase from other organisms are described.

Acinetobacter

Cells of *Acinetobacter calcoaceticus* strain BD413 (ATCC #33305) are grown on ECLB (*E. coli* luria broth), collected during the logarithmic growth phase and washed in a buffer containing; Hepes, pH 7.5, 0.1M NaCl, 1 mM DTT and protease inhibitors. Washed cells were resuspended in fresh buffer and ruptured by passage through a French pressure cell (two passes at ~16,000 p.s.i.). Unbroken cells are removed by centrifugation at 5000 x g for 10 minutes, and membranes are collected by centrifugation at 100,000 x g for 1 hour. The membrane pellet is homogenized in storage buffer (25 mM Hepes, pH 7.5, 10% (w/v) glycerol). Wax synthase activity is detected in these membranes using assay conditions described for the jojoba enzyme in Example 1B, using [1-$^{14}$C] palmitoyl-CoA and 18:1 alcohol as the substrates.

Wax synthase activity is solubilized by incubation of the membranes with 2% CHAPS in the presence of 0.5M NaCl, as described for the jojoba enzyme in Example 4B. Solubilization of the activity is demonstrated by the detection of wax synthase enzyme activity in the supernatant fraction after centrifugation at 200,000 g for 1 hour and by size exclusion chromatography (i.e. the activity elutes from the column in the retained fractions as a symmetrical peak). The activity of the solubilized enzyme is detected by simple dilution of the CHAPS concentration to ~0.3% (i.e. to below its CMC). Incorporation of the enzyme into phospholipid vesicles is not required to detect solubilized activity.

For purification, the solubilized Acinetobacter wax synthase activity is subjected to chromatographic purification procedures similar to those described for the jojoba acyl-CoA reductase. The soluble protein preparation is loaded to a Blue A agarose column under low salt conditions (150 mM NaCl in a column buffer containing 0.75% CHAPS, 10% glycerol, 25 mM Hepes, pH 7.5) and eluted from the column using 1.0M NaCl in the column buffer.

Size exclusion chromatography on Superose 12 (Pharmacia; Piscataway, N.J.) medium is used to obtain an estimate of the size of the native enzyme and to aid in identifying candidate polypeptides. Comparison to molecular mass standards chromatographed under identical conditions yields an estimate of ~46 kD for the native wax synthase activity. Three polypeptides bands, with apparent molecular masses of 45 kD, 58 kD and 64 kD, were identified which tracked with wax synthase activity. N-terminal sequence of the 45 kD polypeptide, the strongest candidate for wax synthase, is determined as XDIAIIGSGsAGLAQaxilkdag, where the one letter code for amino acids is used, "X" represents a position where the amino acid could not be identified, and amino acids represented by lower case letters represent residues which were identified with a lesser degree of confidence. In addition, sequence of a tryptic peptide of the Acinetobacter wax synthase protein is determined as QQFTVWXNASEPS.

Euglena

*Euglena gracilis,* strain Z (ATCC No. 12716) is grown heterotrophically in the dark (Tani et al. (1987) *Agric. Biol. Chem.* 51:225–230) at ~26° C. with moderate shaking. Cells are collected and washed in buffer containing 25 mM Bis-Tris-Propane, pH 7.0, 0.25M NaCl and 1 mM EDTA. Washed cells are resuspended in fresh buffer and ruptured by passage through a French pressure cell (two passes at ~16,000 p.s.i.). Unbroken cells, cell debris and nuclei are removed by centrifugation at 20,000 x g for 20 minutes, and microsomal membranes are collected by centrifugation at 200,000 x g for 1 hour. The membrane pellet is homogenized in storage buffer (25mM Bis-Tris-Propane, pH 7.0, 0.25M NaCl, 10% (w/v) glycerol and 1 mM EDTA ). Wax synthase activity is detected in these membranes using assay conditions as described for the jojoba enzyme. The radiolabelled substrate is the same as for the jojoba example (i.e. [1-$^{14}$C] palmitoyl-CoA), however, 16:0 rather than 18:1 is used as the alcohol acceptor, and Bis-Tris-Propane buffer at pH 7.0 is utilized.

The Euglena wax synthase activity is solubilized by incubation of the membranes with 2% CHAPS in the presence of 0.5M NaCl. Solubilization of the protein is demonstrated by the detection of enzyme activity in the supernatant fraction after centrifugation at 200,000 x g for 1 hour. The activity of the solubilized enzyme is detected by dilution of the CHAPS concentration to ~0.3% (i.e. to below its CMC). It is not necessary to incorporate the enzyme into phospholipid vesicles as was the case for the solubilized jojoba wax synthase.

For partial purification, the solubilized Euglena wax synthase activity is subjected to chromatographic separation on Blue A agarose medium. The column is equilibrated with 0.1M NaCl in a column buffer containing; 25 mM Bis-Tris-Propane, pH 7.0, 20% (w/v) glycerol, 0.75% CHAPS and 1 mM EDTA. The sample containing solubilized wax synthase activity is diluted to 0.1M NaCl and loaded onto a 1×7cm column (5.5 ml bed volume). The column is washed with equilibration buffer and subjected to a linear NaCl gradient (0.1M to 1.0M NaCl) in column buffer. Wax synthase activity is eluted as a broad peak in the last half of the salt gradient.

SDS-PAGE analysis of column fractions reveals that the polypeptide complexity of the activity eluted from the column is greatly reduced relative to the loaded material. A polypeptide with an apparent molecular mass of ~41 kD was observed to track with wax synthase activity in the column fractions. Further purification techniques, such as described for jojoba and Acinetobacter are conducted to verify the association of wax synthase activity with the ~41 kD peptide.

For further analysis of wax synthase activity in Euglena, size exclusion chromatography was conducted as follows. A microsomal membrane preparation was obtained from Euglena cells grown on liquid, heterotrophic, medium (Tani et al., supra) in the dark. Wax synthase activity was solubilized by treating the membranes with 2% (w/v) CHAPS and 500 mM NaCl in a buffered solution (25 mM Bis-Tris, pH 7.0, 1 mM EDTA and 10% (w/v) glycerol) for 1 hour on ice. After dilution of the CHAPS to 0.75% and the NaCl to 200 mM by addition of a dilution buffer, the sample was centrifuged at ~200,000 x g for 1.5 hours. The supernatant fraction was loaded onto a Blue A dye column pre-equilibrated with Column Buffer (25 mM Bis-Tris pH 7.0, 1 mM EDTA, 10% glycerol, 0.75% CHAPS) which also contained 200 mM NaCl. The column was washed with Column Buffer containing 200 mM NaCl until the A280 of the effluent returned to the preload value. Wax synthase activity which had bound to the column was released by increasing the NaCl concentration in the Column Buffer to 1.5M. The fractions from the Blue A column containing wax synthase activity released by the 1.5M NaCl (~20 ml combined volume) were pooled and concentrated approximately 30-fold via ultrafiltration (Amicon pressure cell fitted with a YM 30 membrane). The concentrated material from the Blue A column was used as the sample for a separation via size exclusion chromatography on Superose 12 medium (Pharmacia).

Approximately 200 μl of the sample was loaded onto a Superose 12 column (HR 10/30), pre-equilibrated with Column Buffer containing 0.5M NaCl, and developed at a flow rate of 0.1 ml/min. The wax synthase activity eluted from the column as a smooth peak. Comparison of the elution volume of the wax synthase activity with the elution profiles of molecular mass standard proteins yielded an estimate of 166 kD for the apparent molecular mass of the enzyme. Fractions which contained wax synthase activity were analyzed via SDS-polyacrylamide gel electrophoresis followed by silver staining. A preliminary analysis of the polypeptide profiles of the various fractions did not reveal any proteins with molecular masses of 100 kD or greater whose staining intensity appeared to match the activity profile. The wax synthase polypeptide may be present as a minor component in the sample mixture that is not readily detectable on the silver-stained gel. Alternatively, the enzyme may be composed of subunits which are dissociated during SDS-PAGE.

B. In addition to jojoba reductase, such as that encoded by the sequence provided in FIG. 1, reductase proteins from other sources are also desirable for use in conjunction with the wax synthase proteins of this invention. Such proteins may be identified and obtained from organisms known to produce wax esters from alcohol and acyl substrates.

For example, an NADH-dependent fatty acyl-CoA reductase activity can be obtained from microsomal membranes isolated from *Euglena gracilis.* Methods which may be used to isolate microsomal membranes are described, for example in the published PCT patent application WO 92/14816 (application number PCT/US92/03164, filed Feb. 21, 1992). The reductase activity is solubilized from these membranes using the same approaches as used for jojoba reductase and wax synthase. Membranes are incubated on ice for one hour with various amounts of the detergent, CHAPS, in a buffering solution consisting of 25 mM BisTris, pH 6.9, 250 mM NaCl, 10% glycerol and 1 mM EDTA. The sample is then centrifuged at 200,000 x g for one hour, and the supernatant and pellet fractions assayed for NADH-dependent reductase activity using radiolabeled palmitoly-CoA and NADH as substrates. A convenient assay for reductase activity is described in PCT patent application WO 92/14816. Incubation of the membranes with 0.3, 0.5 or 0.7% (w/v) CHAPS results in retention of reductase activity in the supernatant fractions, indicative of solubilzation of the enzyme. If CHAPS is omitted during the incubation and centrifugation, all of the reductase activity is found in the pellet fraction. All of the samples are diltued ten-fold in this same buffer solution prior to assaying in order to dilute the CHAPS present during the incubation. The presence of CHAPS in the assay at levels above the CMC (approximately 0.5% (w/v) results in inhibition of enzyme activity. Stability of the reductase activity in up to 2% CHAPS may be improved by increasing the glycerol concentration in the buffering solution to 20%. Reductase activity is recovered by dilution of the CHAPS to below the CMC.

Example 7

Isolation of Wax Synthase Nucleic Acid Sequences

Isolation of nucleic acid sequences from cDNA libraries or from genomic DNA is described.

A. Construction of Jojoba cDNA Libraries

RNA is isolated from jojoba embryos collected at 80–90 days post-anthesis using a polyribosome isolation method, initially described by Jackson and Larkins (*Plant Physiol.* (1976) 57:5–10), as modified by Goldberg et al. (*Developmental Biol.* (1981) 83:201–217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000 x g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000 x g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM MgCl2, 5 mM β-mercaptoethanol) is added to each tube. The tubes are placed on ice for 10 minutes, after which the pellets are thoroughly resuspended and pooled. The supernatant is then centrifuged at 120 x g for 10 minutes to remove insoluble material. One volume of self-digested 1 mg/ml proteinase K in 20 mM Tris pH 7.6, 200 mM EDTA, 2% N-lauryl-sarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000 x g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000 x g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

Polyadenylated RNA is used to construct a cDNA library in the plasmid cloning vector pCGN1703, derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA wax synthase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into *E. coli* strain DH5α (BRL, Gaithersburg, Md.) to generate the cDNA library. The jojoba embryo cDNA bank contains between approximately $1.5 \times 10^6$ clones with an average cDNA insert size of approximately 500 base pairs.

Additionally, jojoba polyadenylated RNA is also used to construct a cDNA library in the cloning vector λZAPII/EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately $1 \times 10^6$ clones with an average cDNA insert size of approximately 400 base pairs.

B. Polymerase Chain Reaction

Using amino acid sequence information obtained as described in Example 5, nucleic acid sequences of proteins are obtained by polymerase chain reaction (PCR). Synthetic oligonucleotides are synthesized which correspond to the amino acid sequence of selected peptide fragments. If the order of the fragments in the protein is known, such as when one of the peptides is from the N-terminus or the selected peptides are contained on one long peptide fragment, only one oligonucleotide primer is needed for each selected peptide. The oligonucleotide primer for the more N-terminal peptide, forward primer, contains the encoding sequence for the peptide. The oligonucleotide primer for the more C-terminal peptide, reverse primer, is complementary to the encoding sequence for the selected peptide. Alternatively, when the order of the selected peptides is not known, two oligonucleotide primers are required for each peptide, one encoding the selected amino acid sequence and one complementary to the selected amino acid sequence. Any sequenced peptides may be selected for construction of oligonucleotides, although more desirable peptides are those which contain amino acids which are encoded by the least number of codons, such as methionine, tryptophan, cysteine, and other amino acids encoded by fewer than four codons. Thus, when the oligonucleotides are mixtures of all possible sequences for a selected peptide, the number of degenerate oligonucleotides may be low.

PCR is conducted with these oligonucleotide primers using techniques that are well known to those skilled in the art. Jojoba nucleic acid sequences, such as reverse transcribed cDNA, DNA isolated from the cDNA libraries described above or genomic DNA, are used as template in these reactions. In this manner, segments of DNA are produced. The PCR products are analyzed by gel electrophoresis techniques to select those reactions yielding a desirable fragment.

C. Screening Libraries

DNA fragments obtained by PCR are labeled and used as a probe to screen clones from the cDNA libraries described above. DNA library screening techniques are known to those in the art and described, for example in Maniatis et al. (*Molecular Cloning: A Laboratory Manual, Second Edition* (1989) Cola Spring Harbor Laboratory Press). In this manner, nucleic acid sequences are obtained which may be and used for expression of in various hosts, both procaryotic and eucaryotic.

An approximately 1500 nucleotide jojoba cDNA clone is obtained in this manner. Comparison to the peptide fragments provided in Table 2 reveals the presence of each of these peptides in the translated sequence, with the exception of SQ1129. Northern analysis of jojoba embryo RNA indicates that the mRNA is approximately 2 kb in length. Additional nucleic acid sequence is obtained using further PCR techniques, such as 5' RACE (Frohman et al., *Proc. Nat. Acad. Sci.* (1988) 85:8998–9002). Alternatively, additional sequences may be obtained by rescreening cDNA libraries or from genomic DNA. Preliminary DNA sequence of a jojoba gene is presented in FIG. 2. Further DNA sequence analysis of additional clones indicates that there are at least two classes of jojoba cDNAs. A plasmid containing the entire coding region in pCGN1703 is constructed to contain a SalI site approximately 8 nucleotides 5' to the ATG start codon, and is designated pCGN7614. The complete DNA sequence of pCGN7614 is presented in FIG. 3. The major difference between the two classes of cDNAs as represented in the sequences in FIGS. 2 and 3 is the presence (FIG. 2) or absence (FIG. 3) of the 6 nucleotide coding sequence for amino acids 23 and 24 of FIG. 2.

D. Expression in *E. coli*

The wax synthase gene from pCGN7614 is placed under the control of the Tac promoter of *E. coli* expression vector pDR540 (Pharmacia) as follows. pCGN7614 DNA is digested at the SalI sites and the ends are partially filled in using the Klenow fragment of DNA polymerase I and the nucleotides TTP and dCTP. The pDR540 vector is prepared by digesting with BamHI and partially filling in the ends with dGTP and dATP. The 1.8 kb fragment from pCGN7614 and the digested pDR540 vector are gel purified using low melting temperature agarose and ligated together using T4 DNA ligase. A colony containing the wax synthase in the sense orientation relative to the *E. coli* promoter was designated pCGN7620, and a colony containing the wax synthase gene in the antisense orientation was designated pCGN7621. To assay for wax synthase activity, 50 ml cultures of pCGN7620 and pCGN7621 are grown to log phase in liquid culture, and induced for 2 hours by the addition of IPTG to a concentration of 1 mM. The cells are harvested by centrifugation and subjected to the assay for wax synthase activity as described for jojoba extracts. TLC analysis indicates that the cell extract from pCGN7620 directs synthesis of wax ester, while the control extract from pCGN7621 does not direct the synthesis of wax ester. The wax synthase assay in these harvested cells was verified by a second assay, however, further attempts to produce wax synthase activity in *E. coli* cells have been unsuccessful.

Example 8

Constructs for Plant Expression

Constructs which provide for expression in plant cells may be prepared as follows.

A. Expression Cassettes

Expression cassettes which contain 5' and 3' regulatory regions from genes expressed preferentially in seed tissues may be prepared from napin, Bce4 and ACP genes as described, for example in WO 92/03564.

For example, napin expression cassettes may be prepared as follows. A napin expression cassette, pCGN1808, which may be used for expression of gene constructs is described in Kridl et al. (*Seed Science Research* (1991) 1:209–219), which is incorporated herein by reference.

Alternatively, pCGN1808 may be modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) Gene 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restiction sites as well as nucleotides 408–423 of the napin 5'-sequence (from the EcoRV site) and the reverse primer contains the complement to napin sequences 718–739 which include the unique SacI site in the 5'-promoter. The PCR was performed using a Perkin Elmer/Cetus thermocycler according to manufacturer's specifications. The PCR fragment is subcloned as a blunt-ended fragment into pUC8 (Vieira and Messing (1982) Gene 19:259–268) and digested with HincII to give pCGN3217. Sequence of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1,725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

Similarly, a cassette for cloning of sequences for transcription regulation under the control of 5' and 3' regions from an oleosin gene may be prepared. Sequence of a Brassica napus oleosin gene was reported by Lee and Huang (Plant Phys. (1991) 96:1395–1397). Primers to the published sequence are used in PCR reactions to obtain the 5' and 3' regulatory regions of an oleosin gene from Brassica napus cv. Westar. Two PCR reactions were performed, one to amplify approximately 950 nucleotides immediatley upstream of the ATG start codon for the oleosin gene, and one to PCR amplify approximately 600 bp including and downstream of the TAA stop codon for the oleosin gene. The PCR products were cloned into plasmid vector pAMP1 (BRL) according to manufacturers protocols to yield plasmids pCGN7629 which contains the oleosin 5' flanking region and pCGN7630 which contains the 3' flanking region. The PCR primers included convenient restriction sites for cloning the 5' and 3' flanking regions together into an expression cassette. A PstI fragment containing the 5' flanking region from pCGN7629 was cloned into PstI digested pCGN7630 to yield plasmid pCGN7634. The BssHII (New England BioLabs) fragment from pCGN7634, which contains the entire oleosin expression cassette was cloned into BssHII digested pBCSK+ (Stratagene) to provide the oleosin cassette in a plasmid, pCGN7636. Sequence of the oleosin cassette in pCGN7636 is provided in FIG. 4. The oleosin cassette is flanked by BssHII, KpnI and XbaI restriction sites, and contains SalI, BamHI and PstI sites for insertion of DNA sequences of interest between the 5' and 3' oleosin regions.

Gene sequences are inserted into such cassettes to provide expression constructs for plant transformation methods. For example, such constructs may be inserted into binary vectors for Agrobacterium-mediated transformation as described below.

B. Constructs for Plant Transformation

Plasmid pCGN7614 is digested with AflIII, and ligated with adapters to add BclI sites to the AflIII sticky ends, followed by digestion with SalI and BclI. The fragment containing the gene is gel purified and cloned into SalI/BamHI digested pCGN3223, a napin expression cassette. The resulting plasmid which contains the gene in a sense orientation in the napin expression cassette is designated pCGN7624. DNA isolated from pCGN7624 is digested with Asp718 (a KpnI isoschizimer), and the napin fusion gene is cloned into Asp718 digested binary vector pCGN1578 (McBride and Summerfelt, supra). The resultant binary vector, designated pCGN7626, is transformed into Agrobacterium strain EHA101 and used for transformation of Arabidopsis and rapeseed explants.

Additional binary vectors are prepared from pCGN1578, pCGN1559 and other vectors described by McBride et al. (supra) by substitution of the pCGN1578 and pCGN1559 linker regions with a linker region containing the following restriction digestion sites: Asp718/AscI/PacI/XbaI/BamHI/SwaI/Sse8387 (PstI)/HindIII. This results in pCGN1578PASS or pCGN1559PASS, and other modified vectors which are designated similarly. AscI, PacI, SwaI and Sse8387 have 8-base restriction recognition sites. These enzymes are available from New England BioLabs: AscI, PacI; Boehringer Manheim: SwaI and Takara (Japan): Sse8387.

C. Reductase Constructs for Plant Transformation

Constructs for expression of reductase in plant cells using 5' and 3' regulatory regions from a napin gene, are prepared.

A reductase cDNA (in the pCGN1703 vector described above) designated pCGN7571, is digested with SphI (site in 3' untranslated sequence at bases 1594–1599) and a SalI linker is inserted at this site. The resulting plasmid is digested with BamHI and SalI and the fragment containing the reductase cDNA gel purified and cloned into BglII/XhoI digested pCGN3223, the napin cassette described above, resulting in pCGN7585.

A HindIII fragment of pCGN7585 containing the napin 5'/reductase/napin 3' construct is cloned into HindIII digested pCGN1578 (McBride and Sumerfelt, supra), resulting in pCGN7586, a binary vector for plant transformation.

Plant transformation construct pCGN7589, also containing the jojoba reductase gene under expression of a napin promoter, is prepared as follows. pCGN7571 is in vitro mutagenized to introduce an NdeI site at the first ATG of the reductase coding sequence and a BglII site immediately upstream of the NdeI site. BamHI linkers are introduced into the SphI site downstream of the reductase coding region. The 1.5 kb BglII-BamHI fragment is gel purified and cloned into BglII-BamHI digested pCGN3686 (see below), resulting in pCGN7582.

pCGN3686 is a cloning vector derived from Bluescript KS+ (Stratagene Cloning Systems; San Diego, Calf.), but having a chloramphenicol resistance gene and a modified linker region. The source of the chloramphenicol resistance gene, pCGN565 is a cloning vector based on pUC12-cm (K. Buckley Ph.D. Thesis, Regulation and expression of the phi X174 lysis gene, University of California, San Diego, 1985), but containing pUC18 linkers (Yanisch-Perron, et al., *Gene* (1985) 53:103–119). pCGN565 is digested with HhaI and the fragment containing the chloramphenicol resistance gene is excised, blunted by use of mung bean nuclease, and inserted into the EcoRV site of Bluescript KS- (Stratagene: La Jolla, Calif.) to create pCGN2008. The chloramphenicol resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015. The linker region of pCGN2015 is modified to provide pCGN3686, which contains the following restriction digestion sites, 5' to 3' in the lacZ linker region: PstI, BglII, XhoI, HincII, SalI, HindIII, EcoRV, EcoRI, PstI, SmaI, BamHI, SpeI, XbaI and SacI.

An XhoI linker is inserted at the XbaI site of pCGN7582. The BglII-XhoI fragment containing the reductase gene is isolated and cloned into BglII-XhoI digested pCGN3223. The resulting plasmid, which lacks the 5' untranslated leader sequence from the jojoba gene, is designated pCGN7802. The napin/reductase fragment from pCGN7802 is excised with HindIII and cloned into HindIII digested pCGN1578 to yield pCGN7589.

An additional napin/reductase construct is prepared as follows. The reductase cDNA pCGN7571 (FIG. 1) is mutagenized to insert SalI sites 5' to the ATG start codon (site is 8 base pairs 5' to ATG) and immediately 3' to the TAA translation stop codon, resulting in pCGN7631. pCGN7631 is digested with SalI and the approximately 1.5 kb fragment containing the reductase encoding sequence is cloned into SalI/XhoI digested napin cassette pCGN3223. A resulting plasmid containing the reductase sequence in the sense orientation is designated pCGN7640. pCGN7640 is digested with HindIII, and the fragment containing the oleosin/reductase construct is cloned into HindIII digested binary vector pCGN1559PASS, resulting in binary construct pCGN7642.

A construct for expression of reductase under control of oleosin regulatory regions is prepared as follows. The reductase encoding sequence is obtained by digestion of pCGN7631 with SalI, and ligated into SalI digested pCGN7636, the oleosin cassette. A resulting plasmid containing the reductase sequence in the sense orientation is designated pCGN7641. pCGN7641 is digested with XbaI, and the fragment containing the oleosin/reductase construct is cloned into XbaI digested binary vector pCGN1559PASS, resulting in binary construct pCGN7643.

Binary vector constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187) and used in plant transformation methods as described below.

Example 9

Plant Transformation Methods

A variety of methods have been developed to insert a DNA sequence of interest into the genome of a plant host to obtain the transcription or transcription and translation of the sequence to effect phenotypic changes.

Brassica Transformation

Seeds of high erucic acid, such as cultivar Reston, or Canola-type varieties of Brassica napus are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island,N.Y.) supplemented with pyriodoxine (50 µg/l), nicotinic acid (50 µg/l), glycine (200 µg/l), and 0.6% Phytagar (Gibco) pH 5.8. Seeds are germinated in a Percival chamber at 22° C. in a 16 h photoperiod with cool fluorescent and red light of intensity approximately 65µEinsteins per square meter per second ($\mu Em^{-2}S^{-1}$).

Hypocotyls are excised from 5–7 day old seedlings, cut into pieces approximately 4mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of *A. tumefaciens* strain EHA101 containing a binary plasmid with the desired gene construct are transferred to 5 ml MG/L broth and grown overnight at 30° C. Hypocotyl explants are immersed in 7–12 ml MG/L broth with bacteria diluted to 1×10$^8$ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO^4.7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

Peanut Transformation

DNA sequences of interest may be introduced as expression cassettes, comprising at least a promoter region, a gene of interest, and a termination region, into a plant genome via particle bombardment.

Briefly, tungsten or gold particles of a size ranging from 0.5 mM–3 mM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers. The bombardment of the tissue with the DNA-coated particles is carried out using a Biolistics particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 mM to 300 mM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at $25°\pm 2°$ C. and are subsequently transferred to continuous cool white fluorescent light ($6.8\ W/m^2$). On the 10th day of culture, the plantlets are transferred to pots containing sterile soil, are kept in the shade for 3–5 days are and finally moved to greenhouse. The putative transgenic shoots are rooted. Integration of exogenous DNA into the plant genome may be confirmed by various methods know to those skilled in the art.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

---

What is claimed is:

1. A recombinant DNA construct comprising a nucleic acid sequence which encodes the protein sequence provided in FIG. 2 (SEQ ID NO: 10) or 3 (SEQ ID NO: 11) and a heterologous DNA sequence not naturally associated with said protein encoding sequence.

2. The construct of claim 1 further comprising a promoter which provides for transcription of said encoding sequence in a host cell.

3. The construct of claim 2 wherein said promoter is from a gene expressed in a plant cell.

4. The construct of claim 3 wherein said plant cell is a plant embryo seed cell.

5. The construct of of claim 2 wherein said promoter provides for transcription of said encoding sequence in a bacterial cell.

6. The construct of claim 3 wherein said promoter is from a gene preferentially expressed in a plant seed embryo cell.

7. A Brassica plant cell comprising a recombinant construct comprising a nucleic acid sequence which encodes the protein sequence provided in FIG. 2 (SEQ ID NO: 10) or 3 (SEQ ID NO: 11), wherein said protein encoding sequence is heterologous to said host cell, and wherein said protein encoding sequence is under the regulatory control of a promoter functional in said host cell.

8. A Brassica plant cell comprising a construct according to claim 1.

9. The construct of claim 1 wherein said nucleic acid sequence comprises nucleotides 39–1610 of FIG. 2 (SEQ ID NO: 10) or nucleotides 10–1572 of FIG. 3 (SEQ ID NO: 11).

10. The Brassica plant cell of claim 7 wherein said nucleic acid sequence comprises nucleotides 39–1610 of FIG. 2 (SEQ ID NO: 10) or nucleotides 10–1572 of FIG. 3 (SEQ ID NO: 11).

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1:

```
Glu  Thr  Tyr  Val  Pro  Glu  Ser  Val  Thr  Lys  Lys
 1              5                        10
```

( 2 ) INFORMATION FOR SEQ ID NO: 2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Val  Pro  Xaa  Glu  Pro  Ser  Ile  Ala  Ala  Xaa
 1              5                        10
```

( 2 ) INFORMATION FOR SEQ ID NO: 3:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO: 3:

Glu Thr Tyr Val Pro Glu Glu Val Thr Lys
 1               5                  10

( 2 ) INFORMATION FOR SEQ ID NO: 4:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 4:

Asp Leu Met Ala Val Ala Gly Glu Ala Leu Lys
 1               5                  10

( 2 ) INFORMATION FOR SEQ ID NO: 5:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 5:

Met Thr Asn Val Lys Pro Tyr Ile Pro Asp Phe
 1               5                  10

( 2 ) INFORMATION FOR SEQ ID NO: 6:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 6:

Phe Leu Pro Xaa Xaa Val Ala Ile Thr Gly Glu
 1               5                  10

( 2 ) INFORMATION FOR SEQ ID NO: 7:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 7:

Phe Gly Asn Thr Ser Ser Xaa Xaa Leu Tyr Xaa Glu Leu Ala Tyr Ala
 1               5                  10                  15
Lys ( 2 ) INFORMATION FOR SEQ ID NO: 8:

( i ) SEQUENCE CHARACTERISTICS:
        ( A ) LENGTH: 17 amino acids
        ( B ) TYPE: amino acid
        ( D ) TOPOLOGY: linear (i i) MOLECULE TYPE: peptide (x i) SEQUENCE DESCRIPTION: SEQ ID NO: 8:

| Ala | Glu | Ala | Glu | Glu | Val | Met | Tyr | Gly | Ala | Ile | Asp | Glu | Val | Leu | Glu |
|---|---|---|---|---|---|---|---|---|---|---|---|---|---|---|---|
| 1 | | | | 5 | | | | | 10 | | | | | 15 | |

Lys (2) INFORMATION FOR SEQ ID NO: 9:

(i) SEQUENCE CHARACTERISTICS:
    (A) LENGTH: 1786 base pairs
    (B) TYPE: nucleic acid
    (C) STRANDEDNESS: double
    (D) TOPOLOGY: linear (i i) MOLECULE TYPE: cDNA to mRNA (x i) SEQUENCE DESCRIPTION: SEQ ID NO: 9:

```
AAATCCTCCA CTCATACACT CCACTTCTCT CTCTCTCTCT CTCTCTCTGA AACAATTTGA    60

GTAGCAAACT TAAAAGAAA  ATG GAG GAA ATG GGA AGC ATT TTA GAG TTT CTT   112
                     Met Glu Glu Met Gly Ser Ile Leu Glu Phe Leu
                      1           5                      10

GAT AAC AAA GCC ATT TTG GTC ACT GGT GCT ACT GGC TCC TTA GCA AAA     160
Asp Asn Lys Ala Ile Leu Val Thr Gly Ala Thr Gly Ser Leu Ala Lys
             15              20              25

ATT TTT GTG GAG AAG GTA CTG AGG AGT CAA CCG AAT GTG AAG AAA CTC     208
Ile Phe Val Glu Lys Val Leu Arg Ser Gln Pro Asn Val Lys Lys Leu
         30              35              40

TAT CTT CTT TTG AGA GCA ACC GAT GAC GAG ACA GCT GCT CTA CGC TTG     256
Tyr Leu Leu Leu Arg Ala Thr Asp Asp Glu Thr Ala Ala Leu Arg Leu
     45              50              55

CAA AAT GAG GTT TTT GGA AAA GAG TTG TTC AAA GTT CTG AAA CAA AAT     304
Gln Asn Glu Val Phe Gly Lys Glu Leu Phe Lys Val Leu Lys Gln Asn
 60              65              70              75

TTA GGT GCA AAT TTC TAT TCC TTT GTA TCA GAA AAA GTG ACT GTA GTA     352
Leu Gly Ala Asn Phe Tyr Ser Phe Val Ser Glu Lys Val Thr Val Val
             80              85              90

CCC GGT GAT ATT ACT GGT GAA GAC TTG TGT CTC AAA GAC GTC AAT TTG     400
Pro Gly Asp Ile Thr Gly Glu Asp Leu Cys Leu Lys Asp Val Asn Leu
             95              100             105

AAG GAA GAA ATG TGG AGG GAA ATC GAT GTT GTT GTC AAT CTA GCT GCT     448
Lys Glu Glu Met Trp Arg Glu Ile Asp Val Val Val Asn Leu Ala Ala
         110             115             120

ACA ATC AAC TTC ATT GAA AGG TAC GAC GTG TCT CTG CTT ATC AAC ACA     496
Thr Ile Asn Phe Ile Glu Arg Tyr Asp Val Ser Leu Leu Ile Asn Thr
         125             130             135

TAT GGA GCC AAG TAT GTT TTG GAC TTC GCG AAG AAG TGC AAC AAA TTA     544
Tyr Gly Ala Lys Tyr Val Leu Asp Phe Ala Lys Lys Cys Asn Lys Leu
140             145             150                         155

AAG ATA TTT GTT CAT GTA TCT ACT GCT TAT GTA TCT GGA GAG AAA AAT     592
Lys Ile Phe Val His Val Ser Thr Ala Tyr Val Ser Gly Glu Lys Asn
             160             165             170

GGG TTA ATA CTG GAG AAG CCT TAT TAT ATG GGC GAG TCA CTT AAT GGA     640
Gly Leu Ile Leu Glu Lys Pro Tyr Tyr Met Gly Glu Ser Leu Asn Gly
             175             180             185

AGA TTA GGT CTG GAC ATT AAT GTA GAG AAG AAA CTT GTG GAG GCA AAA     688
Arg Leu Gly Leu Asp Ile Asn Val Glu Lys Lys Leu Val Glu Ala Lys
         190             195             200

ATC AAT GAA CTT CAA GCA GCG GGG GCA ACG GAA AAG TCC ATT AAA TCG     736
Ile Asn Glu Leu Gln Ala Ala Gly Ala Thr Glu Lys Ser Ile Lys Ser
 205             210             215

ACA ATG AAG GAC ATG GGC ATC GAG AGG GCA AGA CAC TGG GGA TGG CCA     784
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Thr | Met | Lys | Asp | Met | Gly | Ile | Glu | Arg | Ala | Arg | His | Trp | Gly | Trp | Pro |      |
| 220 |     |     |     |     | 225 |     |     |     | 230 |     |     |     |     |     | 235 |      |

```
AAT GTG TAT GTA TTC ACC AAG GCA TTA GGG GAG ATG CTT TTG ATG CAA      832
Asn Val Tyr Val Phe Thr Lys Ala Leu Gly Glu Met Leu Leu Met Gln
                    240             245                 250

TAC AAA GGG GAC ATT CCG CTT ACT ATT ATT CGT CCC ACC ATC ATC ACC      880
Tyr Lys Gly Asp Ile Pro Leu Thr Ile Ile Arg Pro Thr Ile Ile Thr
                255             260                 265

AGC ACT TTT AAA GAG CCC TTT CCT GGT TGG GTT GAA GGT GTC AGG ACC      928
Ser Thr Phe Lys Glu Pro Phe Pro Gly Trp Val Glu Gly Val Arg Thr
        270             275                 280

ATC GAT AAT GTA CCT GTA TAT TAT GGT AAA GGG AGA TTG AGG TGT ATG      976
Ile Asp Asn Val Pro Val Tyr Tyr Gly Lys Gly Arg Leu Arg Cys Met
    285             290                 295

CTT TGC GGA CCC AGC ACA ATA ATT GAC CTG ATA CCG GCA GAT ATG GTC     1024
Leu Cys Gly Pro Ser Thr Ile Ile Asp Leu Ile Pro Ala Asp Met Val
300             305                 310                 315

GTG AAT GCA ACG ATA GTA GCC ATG GTG GCG CAC GCA AAC CAA AGA TAC     1072
Val Asn Ala Thr Ile Val Ala Met Val Ala His Ala Asn Gln Arg Tyr
            320             325                 330

GTA GAG CCG GTG ACA TAC CAT GTG GGA TCT TCA GCG GCG AAT CCA ATG     1120
Val Glu Pro Val Thr Tyr His Val Gly Ser Ser Ala Ala Asn Pro Met
                335             340                 345

AAA CTG AGT GCA TTA CCA GAG ATG GCA CAC CGT TAC TTC ACC AAG AAT     1168
Lys Leu Ser Ala Leu Pro Glu Met Ala His Arg Tyr Phe Thr Lys Asn
        350             355                 360

CCA TGG ATC AAC CCG GAT CGC AAC CCA GTA CAT GTG GGT CGG GCT ATG     1216
Pro Trp Ile Asn Pro Asp Arg Asn Pro Val His Val Gly Arg Ala Met
    365             370                 375

GTC TTC TCC TCC TTC TCC ACC TTC CAC CTT TAT CTC ACC CTT AAT TTC     1264
Val Phe Ser Ser Phe Ser Thr Phe His Leu Tyr Leu Thr Leu Asn Phe
380             385                 390                 395

CTC CTT CCT TTG AAG GTA CTG GAG ATA GCA AAT ACA ATA TTC TGC CAA     1312
Leu Leu Pro Leu Lys Val Leu Glu Ile Ala Asn Thr Ile Phe Cys Gln
            400             405                 410

TGG TTC AAG GGT AAG TAC ATG GAT CTT AAA AGG AAG ACG AGG TTG TTG     1360
Trp Phe Lys Gly Lys Tyr Met Asp Leu Lys Arg Lys Thr Arg Leu Leu
        415             420                 425

TTG CGT TTA GTA GAC ATT TAT AAA CCC TAC CTC TTC TTC CAA GGC ATC     1408
Leu Arg Leu Val Asp Ile Tyr Lys Pro Tyr Leu Phe Phe Gln Gly Ile
    430             435                 440

TTT GAT GAC ATG AAC ACT GAG AAG TTG CGG ATT GCT GCA AAA GAA AGC     1456
Phe Asp Asp Met Asn Thr Glu Lys Leu Arg Ile Ala Ala Lys Glu Ser
445             450                 455

ATA GTT GAA GCT GAT ATG TTT TAC TTT GAT CCC AGG GCA ATT AAC TGG     1504
Ile Val Glu Ala Asp Met Phe Tyr Phe Asp Pro Arg Ala Ile Asn Trp
460             465                 470                 475

GAA GAT TAC TTC TTG AAA ACT CAT TTC CCA GGN GTC GTA GAG CAC GTT     1552
Glu Asp Tyr Phe Leu Lys Thr His Phe Pro Gly Val Val Glu His Val
            480             485                 490

CTT AAC  TAAAAGTTAC GGTACGAAAA TGAGAAGATT GGAATGCATG CACCGAAAGN     1608
Leu Asn

NCAACATAAA AGACGTGGTT AAAGTCATGG TCAAAAAGA AATAAATGC AGTTAGGTTT     1668

GTGTTGCAGT TTTGATTCCT TGTATTGTTA CTTGTACTTT TGATCTTTTT CTTTTTTAAT   1728

GAAATTTCTC TCTTTGTTTT GTGAAAAAAA AAAAAAAAAA GAGCTCCTGC AGAAGCTT     1786
```

( 2 ) INFORMATION FOR SEQ ID NO: 10:

( i ) SEQUENCE CHARACTERISTICS:
( A ) LENGTH: 1733 base pairs
( B ) TYPE: nucleic acid
( C ) STRANDEDNESS: double -continued ( D ) TOPOLOGY: linear ( i i ) MOLECULE TYPE: cDNA to mRNA ( x i ) SEQUENCE DESCRIPTION: SEQ ID NO: 10:

| | | | | | | | | | | | | | | | | |
|---|---|---|---|---|---|---|---|---|---|---|---|---|---|---|---|---|
| GGAACTCCAT | CCCTTCCTCC | CTCACTCCTC | TCTCTACA | ATG<br>Met<br>1 | AAG<br>Lys | GCC<br>Ala | AAA<br>Lys | ACA<br>Thr | ATC<br>Ile<br>5 | | | | | | | 56 |
| ACA<br>Thr | AAC<br>Asn | CCG<br>Pro | GAG<br>Glu<br>10 | ATC<br>Ile | CAA<br>Gln | GTC<br>Val | TCC<br>Ser | ACG<br>Thr<br>15 | ACC<br>Thr | ATG<br>Met | ACC<br>Thr | ACC<br>Thr | ACG<br>Thr<br>20 | ACC<br>Thr | ACG<br>Thr | 104 |
| ACT<br>Thr | ATG<br>Met | ACC<br>Thr<br>25 | GCC<br>Ala | ACT<br>Thr | CTC<br>Leu | CCC<br>Pro | AAC<br>Asn<br>30 | TTC<br>Phe | AAG<br>Lys | TCC<br>Ser | TCC<br>Ser | ATC<br>Ile<br>35 | AAC<br>Asn | TTA<br>Leu | CAC<br>His | 152 |
| CAC<br>His | GTC<br>Val<br>40 | AAG<br>Lys | CTC<br>Leu | GGC<br>Gly | TAC<br>Tyr | CAC<br>His<br>45 | TAC<br>Tyr | TTA<br>Leu | ATC<br>Ile | TCC<br>Ser | AAT<br>Asn<br>50 | GCC<br>Ala | CTC<br>Leu | TTC<br>Phe | CTC<br>Leu | 200 |
| GTA<br>Val<br>55 | TTC<br>Phe | ATC<br>Ile | CCC<br>Pro | CTT<br>Leu | TTG<br>Leu<br>60 | GGC<br>Gly | CTC<br>Leu | GCT<br>Ala | TCG<br>Ser | GCC<br>Ala<br>65 | CAT<br>His | CTC<br>Leu | TCC<br>Ser | TCC<br>Ser | TTC<br>Phe<br>70 | 248 |
| TCG<br>Ser | GCC<br>Ala | CAT<br>His | GAC<br>Asp | TTG<br>Leu<br>75 | TCC<br>Ser | CTG<br>Leu | CTC<br>Leu | TTC<br>Phe | GAC<br>Asp<br>80 | CTC<br>Leu | CTT<br>Leu | CGC<br>Arg | CGC<br>Arg | AAC<br>Asn<br>85 | CTC<br>Leu | 296 |
| CTC<br>Leu | CCT<br>Pro | GTT<br>Val | GTC<br>Val<br>90 | GTT<br>Val | TGT<br>Cys | TCT<br>Ser | TTC<br>Phe | CTC<br>Leu<br>95 | TTC<br>Phe | GTT<br>Val | TTA<br>Leu | TTA<br>Leu | GCA<br>Ala<br>100 | ACC<br>Thr | CTA<br>Leu | 344 |
| CAT<br>His | TTC<br>Phe | TTG<br>Leu<br>105 | ACC<br>Thr | CGG<br>Arg | CCC<br>Pro | AGG<br>Arg | AAT<br>Asn<br>110 | GTC<br>Val | TAC<br>Tyr | TTG<br>Leu | GTG<br>Val | GAC<br>Asp<br>115 | TTT<br>Phe | GGA<br>Gly | TGC<br>Cys | 392 |
| TAT<br>Tyr | AAG<br>Lys<br>120 | CCT<br>Pro | CAA<br>Gln | CCG<br>Pro | AAC<br>Asn | CTG<br>Leu<br>125 | ATG<br>Met | ACA<br>Thr | TCC<br>Ser | CAC<br>His | GAG<br>Glu<br>130 | ATG<br>Met | TTC<br>Phe | ATG<br>Met | GAC<br>Asp | 440 |
| CGG<br>Arg<br>135 | ACC<br>Thr | TCC<br>Ser | CGG<br>Arg | GCC<br>Ala | GGG<br>Gly<br>140 | TCG<br>Ser | TTT<br>Phe | TCT<br>Ser | AAG<br>Lys | GAG<br>Glu<br>145 | AAT<br>Asn | ATT<br>Ile | GAG<br>Glu | TTT<br>Phe | CAG<br>Gln<br>150 | 488 |
| AGG<br>Arg | AAG<br>Lys | ATC<br>Ile | TTG<br>Leu | GAG<br>Glu<br>155 | AGG<br>Arg | GCC<br>Ala | GGT<br>Gly | ATG<br>Met | GGT<br>Gly<br>160 | CGG<br>Arg | GAA<br>Glu | ACC<br>Thr | TAT<br>Tyr | GTC<br>Val<br>165 | CCC<br>Pro | 536 |
| GAA<br>Glu | TCC<br>Ser | GTC<br>Val | ACT<br>Thr<br>170 | AAG<br>Lys | GTG<br>Val | CCC<br>Pro | GCC<br>Ala | GAG<br>Glu<br>175 | CCG<br>Pro | AGC<br>Ser | ATA<br>Ile | GCA<br>Ala | GCA<br>Ala<br>180 | GCC<br>Ala | AGG<br>Arg | 584 |
| GCC<br>Ala | GAG<br>Glu | GCG<br>Ala<br>185 | GAG<br>Glu | GAG<br>Glu | GTG<br>Val | ATG<br>Met | TAC<br>Tyr<br>190 | GGG<br>Gly | GCG<br>Ala | ATC<br>Ile | GAC<br>Asp | GAG<br>Glu<br>195 | GTG<br>Val | TTG<br>Leu | GAG<br>Glu | 632 |
| AAG<br>Lys | ACG<br>Thr<br>200 | GGG<br>Gly | GTG<br>Val | AAG<br>Lys | CCG<br>Pro | AAG<br>Lys<br>205 | CAG<br>Gln | ATA<br>Ile | GGA<br>Gly | ATA<br>Ile | CTG<br>Leu<br>210 | GTG<br>Val | GTG<br>Val | ANC<br>Xxx | TGC<br>Cys | 680 |
| AGC<br>Ser<br>215 | TTG<br>Leu | TTT<br>Phe | AAC<br>Asn | CCA<br>Pro | ACG<br>Thr<br>220 | CCG<br>Pro | TCG<br>Ser | CTG<br>Leu | TCA<br>Ser | TCC<br>Ser<br>225 | ATG<br>Met | ATA<br>Ile | GTT<br>Val | AAC<br>Asn | CAT<br>His<br>230 | 728 |
| TAC<br>Tyr | AAG<br>Lys | CTN<br>Leu | AGG<br>Arg | GGT<br>Gly<br>235 | AAT<br>Asn | ATA<br>Ile | CTT<br>Leu | AGC<br>Ser | TAT<br>Tyr<br>240 | AAT<br>Asn | CTT<br>Leu | GGT<br>Gly | GGC<br>Gly | ATG<br>Met<br>245 | GGT<br>Gly | 776 |
| TGC<br>Cys | AGT<br>Ser | GCT<br>Ala | GGG<br>Gly<br>250 | CTC<br>Leu | ATT<br>Ile | TCC<br>Ser | ATT<br>Ile | GAT<br>Asp<br>255 | CTT<br>Leu | GCC<br>Ala | AAG<br>Lys | GAC<br>Asp | CTC<br>Leu<br>260 | CTA<br>Leu | CAG<br>Gln | 824 |
| GTT<br>Val | TAC<br>Tyr | CGT<br>Arg<br>265 | AAA<br>Lys | AAC<br>Asn | ACA<br>Thr | TAT<br>Tyr | GTG<br>Val<br>270 | TTA<br>Leu | GTA<br>Val | GTG<br>Val | AGC<br>Ser | ACG<br>Thr<br>275 | GAA<br>Glu | AAC<br>Asn | ATG<br>Met | 872 |
| ACC<br>Thr | CTT<br>Leu | AAT<br>Asn<br>280 | TGG<br>Trp | TAC<br>Tyr | TGG<br>Trp | GGC<br>Gly<br>285 | AAT<br>Asn | GAC<br>Asp | CGC<br>Arg | TCC<br>Ser | ATG<br>Met<br>290 | CTT<br>Leu | ATC<br>Ile | ACC<br>Thr | AAC<br>Asn | 920 |

| | | | | | | | | | | | | | | | | |
|---|---|---|---|---|---|---|---|---|---|---|---|---|---|---|---|---|
| TGC | CTA | TTT | CGC | ATG | GGT | GGC | GCT | GCC | ATC | ATC | CTC | TCA | AAC | CGC | TGG | 968 |
| Cys | Leu | Phe | Arg | Met | Gly | Gly | Ala | Ala | Ile | Ile | Leu | Ser | Asn | Arg | Trp | |
| 295 | | | | 300 | | | | | 305 | | | | | | 310 | |
| CGT | GAT | CGT | CGC | CGA | TCC | AAG | TAC | CAA | CTC | CTT | CAT | ACA | GTA | CGC | ACC | 1016 |
| Arg | Asp | Arg | Arg | Arg | Ser | Lys | Tyr | Gln | Leu | Leu | His | Thr | Val | Arg | Thr | |
| | | | | 315 | | | | | 320 | | | | | 325 | | |
| CAC | AAG | GGC | GCT | GAC | GAC | AAG | TCC | TAT | AGA | TGC | GTC | TTA | CAA | CAA | GAA | 1064 |
| His | Lys | Gly | Ala | Asp | Asp | Lys | Ser | Tyr | Arg | Cys | Val | Leu | Gln | Gln | Glu | |
| | | | 330 | | | | | 335 | | | | | 340 | | | |
| GAT | GAA | AAT | AAC | AAG | GTA | GGT | GTT | GCC | TTA | TCC | AAG | GAT | CTG | ATG | GCA | 1112 |
| Asp | Glu | Asn | Asn | Lys | Val | Gly | Val | Ala | Leu | Ser | Lys | Asp | Leu | Met | Ala | |
| | | 345 | | | | 350 | | | | | 355 | | | | | |
| GTT | GCC | GGT | GAA | GCC | CTA | AAG | GCC | AAC | ATC | ACG | ACC | CTT | GGT | CCC | CTC | 1160 |
| Val | Ala | Gly | Glu | Ala | Leu | Lys | Ala | Asn | Ile | Thr | Thr | Leu | Gly | Pro | Leu | |
| | 360 | | | | | 365 | | | | | 370 | | | | | |
| GTG | CTC | CCC | ATG | TCA | GAA | CAA | CTC | CTC | TTC | TTT | GCC | ACC | TTA | GTG | GCA | 1208 |
| Val | Leu | Pro | Met | Ser | Glu | Gln | Leu | Leu | Phe | Phe | Ala | Thr | Leu | Val | Ala | |
| 375 | | | | | 380 | | | | | 385 | | | | | 390 | |
| CGT | AAG | GTC | TTC | AAG | ATG | ACG | AAC | GTG | AAG | CCA | TAC | ATC | CCA | GAT | TTC | 1256 |
| Arg | Lys | Val | Phe | Lys | Met | Thr | Asn | Val | Lys | Pro | Tyr | Ile | Pro | Asp | Phe | |
| | | | | 395 | | | | | 400 | | | | | 405 | | |
| AAG | TTG | GCA | GCG | AAC | GAC | TTC | TGC | ATC | CAT | GCA | GGA | GGC | AAA | GCA | GTG | 1304 |
| Lys | Leu | Ala | Ala | Asn | Asp | Phe | Cys | Ile | His | Ala | Gly | Gly | Lys | Ala | Val | |
| | | | 410 | | | | | 415 | | | | | 420 | | | |
| TTG | GAT | GAG | CTC | GAG | AAG | AAC | TTG | GAG | TTG | ACG | CCA | TGG | CAC | CTT | GAA | 1352 |
| Leu | Asp | Glu | Leu | Glu | Lys | Asn | Leu | Glu | Leu | Thr | Pro | Trp | His | Leu | Glu | |
| | | 425 | | | | | 430 | | | | | 435 | | | | |
| CCC | TCG | AGG | ATG | ACA | CTG | TAT | AGG | TTT | GGG | AAC | ACA | TCG | AGT | AGC | TCA | 1400 |
| Pro | Ser | Arg | Met | Thr | Leu | Tyr | Arg | Phe | Gly | Asn | Thr | Ser | Ser | Ser | Ser | |
| | 440 | | | | | 445 | | | | | 450 | | | | | |
| TTA | TGG | TAC | GAG | TTG | GCA | TAC | GCT | GAA | GCA | AAA | GGG | AGG | ATC | CGT | AAG | 1448 |
| Leu | Trp | Tyr | Glu | Leu | Ala | Tyr | Ala | Glu | Ala | Lys | Gly | Arg | Ile | Arg | Lys | |
| 455 | | | | | 460 | | | | | 465 | | | | | 470 | |
| GGT | GAT | CGA | ACT | TGG | ATG | ATT | GGA | TTT | GGT | TCA | GGT | TTC | AAG | TGT | AAC | 1496 |
| Gly | Asp | Arg | Thr | Trp | Met | Ile | Gly | Phe | Gly | Ser | Gly | Phe | Lys | Cys | Asn | |
| | | | | 475 | | | | 480 | | | | | 485 | | | |
| AGT | GTT | GTG | TGG | AGG | GCT | TTG | AGG | AGT | GTC | AAT | CCG | GCT | AGA | GAG | AAG | 1544 |
| Ser | Val | Val | Trp | Arg | Ala | Leu | Arg | Ser | Val | Asn | Pro | Ala | Arg | Glu | Lys | |
| | | | 490 | | | | | 495 | | | | | 500 | | | |
| AAT | CCT | TGG | ATG | GAT | GAA | ATT | GAG | AAG | TTC | CCT | GTC | CAT | GTG | CCT | AAA | 1592 |
| Asn | Pro | Trp | Met | Asp | Glu | Ile | Glu | Lys | Phe | Pro | Val | His | Val | Pro | Lys | |
| | | 505 | | | | | 510 | | | | | 515 | | | | |
| ATC | GCA | CCT | ATC | GCT | TCG | TAGAACTGCT | AGGATGTGAT | TAGTAATGAA | | | | | | | | 1640 |
| Ile | Ala | Pro | Ile | Ala | Ser | | | | | | | | | | | |
| | | 520 | | | | | | | | | | | | | | |

AAATGTGTAT TATGTTAGTG ATGTAGAAAA AGAAACTTTA GTTGATGGGT GAGAACATGT 1700

CTCATTGAGA ATAACGTGTG CATCGTTGTG TTG 1733

( 2 ) INFORMATION FOR SEQ ID NO: 11:

( i ) SEQUENCE CHARACTERISTICS:
        ( A ) LENGTH: 1783 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 11:

| | | | | | | | | | | | |
|---|---|---|---|---|---|---|---|---|---|---|---|
| GTCGACACA | ATG | AAG | GCC | AAA | ACA | ATC | ACA | AAC | CCG | GAG | ATC | CAA | GTC | TCC | 51 |
| | Met | Lys | Ala | Lys | Thr | Ile | Thr | Asn | Pro | Glu | Ile | Gln | Val | Ser | |
| | 1 | | | 5 | | | | | 10 | | | | | | |

| | | | | | | | | | | |
|---|---|---|---|---|---|---|---|---|---|---|
| ACG | ACC | ATG | ACC | ACC | ACG | ACC | ACG | ACC | GCC | ACT | CTC | CCC | AAC | TTC | AAG | 99 |

| | | | | | | | | | | | | | | | | |
|---|---|---|---|---|---|---|---|---|---|---|---|---|---|---|---|---|
| Thr | Thr | Met | Thr | Thr | Thr | Thr | Thr | Thr | Ala | Thr | Leu | Pro | Asn | Phe | Lys | |
| 15 | | | | 20 | | | | 25 | | | | | | | 30 | |

| TCC | TCC | ATC | AAC | TTA | CAC | CAC | GTC | AAG | CTC | GGC | TAC | CAC | TAC | TTA | ATC | 147 |
|---|---|---|---|---|---|---|---|---|---|---|---|---|---|---|---|---|
| Ser | Ser | Ile | Asn | Leu | His | His | Val | Lys | Leu | Gly | Tyr | His | Tyr | Leu | Ile | |
| | | | | 35 | | | | 40 | | | | | | 45 | | |

| TCC | AAT | GCC | CTC | TTC | CTC | GTA | TTC | ATC | CCC | CTT | TTG | GGC | CTC | GCT | TCG | 195 |
|---|---|---|---|---|---|---|---|---|---|---|---|---|---|---|---|---|
| Ser | Asn | Ala | Leu | Phe | Leu | Val | Phe | Ile | Pro | Leu | Leu | Gly | Leu | Ala | Ser | |
| | | | 50 | | | | | 55 | | | | | 60 | | | |

| GCC | CAC | CTC | TCC | TCC | TTC | TCG | GCC | CAT | GAC | TTG | TCC | CTG | CTC | TTC | GAC | 243 |
|---|---|---|---|---|---|---|---|---|---|---|---|---|---|---|---|---|
| Ala | His | Leu | Ser | Ser | Phe | Ser | Ala | His | Asp | Leu | Ser | Leu | Leu | Phe | Asp | |
| | | 65 | | | | | 70 | | | | | 75 | | | | |

| CTC | CTT | CGC | CGC | AAC | CTC | CTC | CCC | GTT | GTC | GTT | TGT | TCT | TTC | CTC | TTC | 291 |
|---|---|---|---|---|---|---|---|---|---|---|---|---|---|---|---|---|
| Leu | Leu | Arg | Arg | Asn | Leu | Leu | Pro | Val | Val | Val | Cys | Ser | Phe | Leu | Phe | |
| | 80 | | | | | 85 | | | | | 90 | | | | | |

| GTT | TTA | TTA | GCA | ACC | CTA | CAT | TTC | TTG | ACC | CGG | CCT | AGG | AAT | GTC | TAC | 339 |
|---|---|---|---|---|---|---|---|---|---|---|---|---|---|---|---|---|
| Val | Leu | Leu | Ala | Thr | Leu | His | Phe | Leu | Thr | Arg | Pro | Arg | Asn | Val | Tyr | |
| 95 | | | | | 100 | | | | | 105 | | | | | 110 | |

| TTG | GTG | GAC | TTT | GCC | TGC | TAT | AAG | CCT | CAC | CCG | AAC | CTG | ATA | ACA | TCC | 387 |
|---|---|---|---|---|---|---|---|---|---|---|---|---|---|---|---|---|
| Leu | Val | Asp | Phe | Ala | Cys | Tyr | Lys | Pro | His | Pro | Asn | Leu | Ile | Thr | Ser | |
| | | | | 115 | | | | | 120 | | | | | 125 | | |

| CAC | GAG | ATG | TTC | ATG | GAC | CGG | ACC | TCC | CGG | GCC | GGG | TCG | TTT | TCT | AAG | 435 |
|---|---|---|---|---|---|---|---|---|---|---|---|---|---|---|---|---|
| His | Glu | Met | Phe | Met | Asp | Arg | Thr | Ser | Arg | Ala | Gly | Ser | Phe | Ser | Lys | |
| | | | 130 | | | | | 135 | | | | | 140 | | | |

| GAG | AAT | ATT | GAG | TTT | CAG | AGG | AAG | ATC | TTG | GAG | AGG | GCC | GGT | ATG | GGC | 483 |
|---|---|---|---|---|---|---|---|---|---|---|---|---|---|---|---|---|
| Glu | Asn | Ile | Glu | Phe | Gln | Arg | Lys | Ile | Leu | Glu | Arg | Ala | Gly | Met | Gly | |
| | | 145 | | | | | 150 | | | | | 155 | | | | |

| CGG | GAA | ACC | TAC | GTC | CCC | GAA | TCC | GTC | ACT | AAG | GTG | CCG | CCC | GAG | CCG | 531 |
|---|---|---|---|---|---|---|---|---|---|---|---|---|---|---|---|---|
| Arg | Glu | Thr | Tyr | Val | Pro | Glu | Ser | Val | Thr | Lys | Val | Pro | Pro | Glu | Pro | |
| 160 | | | | | 165 | | | | | 170 | | | | | | |

| AGC | ATA | GCA | GCA | GCC | AGG | GCC | GAG | GCG | GAG | GAG | GTG | ATG | TAC | GGG | GCG | 579 |
|---|---|---|---|---|---|---|---|---|---|---|---|---|---|---|---|---|
| Ser | Ile | Ala | Ala | Ala | Arg | Ala | Glu | Ala | Glu | Glu | Val | Met | Tyr | Gly | Ala | |
| 175 | | | | | 180 | | | | | 185 | | | | | 190 | |

| ATC | GAC | GAG | GTG | TTG | GAG | AAG | ACG | GGG | GTG | AAG | CCG | AAG | CAG | ATA | GGA | 627 |
|---|---|---|---|---|---|---|---|---|---|---|---|---|---|---|---|---|
| Ile | Asp | Glu | Val | Leu | Glu | Lys | Thr | Gly | Val | Lys | Pro | Lys | Gln | Ile | Gly | |
| | | | | 195 | | | | | 200 | | | | | 205 | | |

| ATA | CTG | GTG | GTG | AAC | TGC | AGC | TTG | TTT | AAC | CCA | ACG | CCG | TCG | CTG | TCA | 675 |
|---|---|---|---|---|---|---|---|---|---|---|---|---|---|---|---|---|
| Ile | Leu | Val | Val | Asn | Cys | Ser | Leu | Phe | Asn | Pro | Thr | Pro | Ser | Leu | Ser | |
| | | | 210 | | | | | 215 | | | | | 220 | | | |

| TCC | ATG | ATA | GTT | AAC | CAT | TAC | AAG | CTT | AGG | GGT | AAT | ATA | CTT | AGC | TAT | 723 |
|---|---|---|---|---|---|---|---|---|---|---|---|---|---|---|---|---|
| Ser | Met | Ile | Val | Asn | His | Tyr | Lys | Leu | Arg | Gly | Asn | Ile | Leu | Ser | Tyr | |
| | | 225 | | | | | 230 | | | | | 235 | | | | |

| AAT | CTT | GGT | GGC | ATG | GGT | TGC | AGT | GCT | GGG | CTC | ATT | TCC | ATT | GAT | CTT | 771 |
|---|---|---|---|---|---|---|---|---|---|---|---|---|---|---|---|---|
| Asn | Leu | Gly | Gly | Met | Gly | Cys | Ser | Ala | Gly | Leu | Ile | Ser | Ile | Asp | Leu | |
| | 240 | | | | | 245 | | | | | 250 | | | | | |

| GCC | AAG | GAC | CTC | CTA | CAG | GTT | TAC | CGT | AAC | ACA | TAT | GTG | TTA | GTA | GTG | 819 |
|---|---|---|---|---|---|---|---|---|---|---|---|---|---|---|---|---|
| Ala | Lys | Asp | Leu | Leu | Gln | Val | Tyr | Arg | Asn | Thr | Tyr | Val | Leu | Val | Val | |
| 255 | | | | | 260 | | | | | 265 | | | | | 270 | |

| AGC | ACA | GAA | AAC | ATG | ACC | CTT | AAT | TGG | TAC | TGG | GGC | AAT | GAC | CGC | TCC | 867 |
|---|---|---|---|---|---|---|---|---|---|---|---|---|---|---|---|---|
| Ser | Thr | Glu | Asn | Met | Thr | Leu | Asn | Trp | Tyr | Trp | Gly | Asn | Asp | Arg | Ser | |
| | | | | 275 | | | | | 280 | | | | | 285 | | |

| ATG | CTT | ATC | ACC | AAC | TGC | CTA | TTT | CGC | ATG | GGT | GGC | GCT | GCC | ATC | ATC | 915 |
|---|---|---|---|---|---|---|---|---|---|---|---|---|---|---|---|---|
| Met | Leu | Ile | Thr | Asn | Cys | Leu | Phe | Arg | Met | Gly | Gly | Ala | Ala | Ile | Ile | |
| | | | 290 | | | | | 295 | | | | | 300 | | | |

| CTC | TCA | AAC | CGC | TGG | CGT | GAT | CGT | CGC | CGA | TCC | AAG | TAC | CAA | CTC | CTT | 963 |
|---|---|---|---|---|---|---|---|---|---|---|---|---|---|---|---|---|
| Leu | Ser | Asn | Arg | Trp | Arg | Asp | Arg | Arg | Arg | Ser | Lys | Tyr | Gln | Leu | Leu | |
| | | 305 | | | | | 310 | | | | | 315 | | | | |

| CAC | ACA | GTA | CGC | ACC | CAC | AAG | GGC | GCT | GAC | GAC | AAG | TCC | TAT | AGA | TGC | 1011 |
|---|---|---|---|---|---|---|---|---|---|---|---|---|---|---|---|---|
| His | Thr | Val | Arg | Thr | His | Lys | Gly | Ala | Asp | Asp | Lys | Ser | Tyr | Arg | Cys | |
| | 320 | | | | | 325 | | | | | 330 | | | | | |

| GTC | TTA | CAA | CAA | GAA | GAT | GAA | AAT | AAC | AAG | GTA | GGT | GTT | GCC | TTA | TCC | 1059 |
|---|---|---|---|---|---|---|---|---|---|---|---|---|---|---|---|---|
| Val | Leu | Gln | Gln | Glu | Asp | Glu | Asn | Asn | Lys | Val | Gly | Val | Ala | Leu | Ser | |
| 335 | | | | | 340 | | | | | 345 | | | | | 350 | |

-continued

| | | | | | | | | | | | | | | | | |
|---|---|---|---|---|---|---|---|---|---|---|---|---|---|---|---|---|
| AAG | GAT | CTG | ATG | GCA | GTT | GCC | GGT | GAA | GCC | CTA | AAG | GCC | AAC | ATC | ACG | 1107 |
| Lys | Asp | Leu | Met | Ala | Val | Ala | Gly | Glu | Ala | Leu | Lys | Ala | Asn | Ile | Thr | |
| | | | | 355 | | | | 360 | | | | | | 365 | | |
| ACC | CTT | GGT | CCC | CTC | GTG | CTC | CCC | ATG | TCA | GAA | CAA | CTC | CTC | TTC | TTT | 1155 |
| Thr | Leu | Gly | Pro | Leu | Val | Leu | Pro | Met | Ser | Glu | Gln | Leu | Leu | Phe | Phe | |
| | | | 370 | | | | | 375 | | | | | 380 | | | |
| GCC | ACC | TTA | GTG | GCA | CGT | AAG | GTC | TTC | AAG | ATG | ACG | AAC | GTG | AAG | CCA | 1203 |
| Ala | Thr | Leu | Val | Ala | Arg | Lys | Val | Phe | Lys | Met | Thr | Asn | Val | Lys | Pro | |
| | | 385 | | | | | 390 | | | | | 395 | | | | |
| TAC | ATC | CCA | GAT | TTC | AAG | TTG | GCA | GCG | AAG | CAC | TTC | TGC | ATC | CAT | GCA | 1251 |
| Tyr | Ile | Pro | Asp | Phe | Lys | Leu | Ala | Ala | Lys | His | Phe | Cys | Ile | His | Ala | |
| | 400 | | | | 405 | | | | | 410 | | | | | | |
| GGA | GGC | AAA | GCA | GTG | TTG | GAT | GAG | CTC | GAG | ACG | AAC | TTG | GAG | TTG | ACG | 1299 |
| Gly | Gly | Lys | Ala | Val | Leu | Asp | Glu | Leu | Glu | Thr | Asn | Leu | Glu | Leu | Thr | |
| 415 | | | | 420 | | | | | 425 | | | | | 430 | | |
| CCA | TGG | CAC | CTT | GAA | CCC | TCG | AGG | ATG | ACA | CTG | TAT | AGG | TTT | GGG | AAC | 1347 |
| Pro | Trp | His | Leu | Glu | Pro | Ser | Arg | Met | Thr | Leu | Tyr | Arg | Phe | Gly | Asn | |
| | | | | 435 | | | | 440 | | | | | 445 | | | |
| ACA | TCG | AGT | AGC | TCA | TTA | TGG | TAC | GAG | TTG | GCA | TAC | GCT | GAA | GCA | AAA | 1395 |
| Thr | Ser | Ser | Ser | Ser | Leu | Trp | Tyr | Glu | Leu | Ala | Tyr | Ala | Glu | Ala | Lys | |
| | | | 450 | | | | 455 | | | | 460 | | | | | |
| GGG | AGG | ATC | CGT | AAG | GGT | GAT | CGA | ACT | TGG | ATG | ATT | GGA | TTT | GGT | TCA | 1443 |
| Gly | Arg | Ile | Arg | Lys | Gly | Asp | Arg | Thr | Trp | Met | Ile | Gly | Phe | Gly | Ser | |
| | | 465 | | | | | 470 | | | | | 475 | | | | |
| GGT | TTC | AAG | TGT | AAC | AGT | GTT | GTG | TGG | AGG | GCT | TTG | AGG | AGT | GTC | AAT | 1491 |
| Gly | Phe | Lys | Cys | Asn | Ser | Val | Val | Trp | Arg | Ala | Leu | Arg | Ser | Val | Asn | |
| | 480 | | | | | 485 | | | | | 490 | | | | | |
| CCG | GCT | AGA | GAG | AAG | AAT | CCT | TGG | ATG | GAT | GAA | ATT | GAG | AAT | TTC | CCT | 1539 |
| Pro | Ala | Arg | Glu | Lys | Asn | Pro | Trp | Met | Asp | Glu | Ile | Glu | Asn | Phe | Pro | |
| 495 | | | | | 500 | | | | | 505 | | | | | 510 | |
| GTC | CAT | GTG | CCT | AAA | ATC | GCA | CCT | ATC | GCT | TCG | TAGAACTGCT | | | AGGATGTGAT | | 1592 |
| Val | His | Val | Pro | Lys | Ile | Ala | Pro | Ile | Ala | Ser | | | | | | |
| | | | 515 | | | | | 520 | | | | | | | | |

| | | | | |
|---|---|---|---|---|
| TAGTAATGAA | AAATGTGTAT | TATGTTAGTG | ATGTAGAAAA | AGAAACTTTA | GTTGATGGGT | 1652 |
| GAGAACATGT | CTCATTGAGA | ATAACGTGTG | CATCGTTGTG | TTGAATTTGA | ATTTGAGTAT | 1712 |
| TGGTGAAATT | CTGTTAGAAT | TGACGCATGA | GTCATATATA | TACAAATTTA | AGTAAGATTT | 1772 |
| TACGCTTTCT | T | | | | | 1783 |

( 2 ) INFORMATION FOR SEQ ID NO: 12:

( i ) SEQUENCE CHARACTERISTICS:
        ( A ) LENGTH: 1647 base pairs
        ( B ) TYPE: nucleic acid
        ( C ) STRANDEDNESS: double
        ( D ) TOPOLOGY: linear ( i i ) MOLECULE TYPE: genomic DNA
        ( A DESCRIPTION: Expression cassette: 5 and 3
        oleosin regulatory regions with restriction sites
        for insertion of genes of interest ( x i ) SEQUENCE DESCRIPTION: SEQ ID NO: 12:

| | | | | | |
|---|---|---|---|---|---|
| GGCGCGCCGG | TACCTCTAGA | CCTGGCGATT | CAACGTGGTC | GGATCATGAC | GCTTCCAGAA | 60 |
| AACATCGAGC | AAGCTCTCAA | AGCTGACCTC | TTTCGGATCG | TACTGAACCC | GAACAATCTC | 120 |
| GTTATGTCCC | GTCGTCTCCG | AACAGACATC | CTCGTAGCTC | GGATTATCGA | CGAATCCATG | 180 |
| GCTATACCCA | ACCTCCGTCT | TCGTCACGCC | TGGAACCCTC | TGGTACGCCA | ATTCCGCTCC | 240 |
| CCAGAAGCAA | CCGGCGCCGA | ATTGCGCGAA | TTGCTGACCT | GGAGACGGAA | CATCGTCGTC | 300 |
| GGGTCCTTGC | GCGATTGCGG | CGGAAGCCGG | GTCGGGTTGG | GGACGAGACC | CGAATCCGAG | 360 |
| CCTGGTGAAG | AGGTTGTTCA | TCGGAGATTT | ATAGACGGAG | ATGGATCGAG | CGGTTTTGGG | 420 |

```
GAAAGGGGAA  GTGGGTTTGG  CTCTTTTGGA  TAGAGAGAGT  GCAGCTTTGG  AGAGAGACTG    480
GAGAGGTTTA  GAGAGAGACG  CGGCGGATAT  TACCGGAGGA  GAGGCGACGA  GAGATAGCAT    540
TATCGAAGGG  GAGGGAGAAA  GAGTGACGTG  GAGAAATAAG  AAACCGTTAA  GAGTCGGATA    600
TTTATCATAT  TAAAAGCCCA  ATGGGCCTGA  ACCCATTTAA  ACAAGACAGA  TAAATGGGCC    660
GTGTGTTAAG  TTAACAGAGT  GTTAACGTTC  GGTTTCAAAT  GCCAACGCCA  TAGGAACAAA    720
ACAAACGTGT  CCTCAAGTAA  ACCCCTGCCG  TTTACACCTC  AATGGCTGCA  TGGTGAAGCC    780
ATTAACACGT  GGCGTAGGAT  GCATGACGAC  GCCATTGACA  CCTGACTCTC  TTCCCTTCTC    840
TTCATATATC  TCTAATCAAT  TCAACTACTC  ATTGTCATAG  CTATTCGGAA  AATACATACA    900
CATCCTTTTC  TCTTCGATCT  CTCTCAATTC  ACAAGAAGCA  AAGTCGACGG  ATCCCTGCAG    960
TAAATTACGC  CATGACTATT  TTCATAGTCC  AATAAGGCTG  ATGTCGGGAG  TCCAGTTTAT   1020
GAGCAATAAG  GTGTTTAGAA  TTTGATCAAT  GTTTATAATA  AAAGGGGGAA  GATGATATCA   1080
CAGTCTTTTG  TTCTTTTTGG  CTTTTGTTAA  ATTTGTGTGT  TTCTATTTGT  AAACCTCCTG   1140
TATATGTTGT  ACTTCTTTCC  CTTTTTAAGT  GGTATCGTCT  ATATGGTAAA  ACGTTATGTT   1200
TGGTCTTTCC  TTTTCTCTGT  TTAGGATAAA  AAGACTGCAT  GTTTATCTT   TAGTTATATT   1260
ATGTTGAGTA  AATGAACTTT  CATAGATCTG  GTTCCGTAGA  GTAGACTAGC  AGCCGAGCTG   1320
AGCTGAACTG  AACAGCTGGC  AATGTGAACA  CTGGATGCAA  GATCAGATGT  GAAGATCTCT   1380
AATATGGTGG  TGGGATTGAA  CATATCGTGT  CTATATTTTT  GTTGGCATTA  AGCTCTTAAC   1440
ATAGATATAA  CTGATGCAGT  CATTGGTTCA  TACACATATA  TAGTAAGGAA  TTACAATGGC   1500
AACCCAAACT  TCAAAACAG   TAGGCCACCT  GAATTGCCTT  ATCGAATAAG  AGTTTGTTTC   1560
CCCCCACTTC  ATGGGATGTA  ATACATGGGA  TTTGGGAGTT  TGAATGAACG  TTGAGACATG   1620
GCAGAACCTC  TAGAGGTACC  GGCGCGC                                         1647
```